(12) United States Patent
Tabolina et al.

(10) Patent No.: US 7,476,531 B2
(45) Date of Patent: Jan. 13, 2009

(54) METHOD FOR PRODUCING L-AMINO ACID USING BACTERIA BELONGING TO THE GENUS ESCHERICHIA

(75) Inventors: Ekaterina Aleksandrovna Tabolina, Moscow (RU); Konstantin Vyacheslavovich Rybak, Moscow (RU); Evgeni Moiseevich Khourges, Moscow (RU); Elvira Borisovna Voroshilova, Moscow (RU); Mikhail Markovich Gusyatiner, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/073,293

(22) Filed: Feb. 13, 2002

(65) Prior Publication Data
US 2005/0239175 A1   Oct. 27, 2005

(30) Foreign Application Priority Data

| Feb. 13, 2001 | (RU) | ............................ 2001103865 |
| Feb. 26, 2001 | (RU) | ............................ 2001104998 |
| Feb. 26, 2001 | (RU) | ............................ 2001104999 |
| Jun. 28, 2001 | (RU) | ............................ 2001117632 |
| Jun. 28, 2001 | (RU) | ............................ 2001117633 |

(51) Int. Cl.
*C12N 1/21* (2006.01)
(52) U.S. Cl. .............................. 435/252.33; 435/252.8; 435/107; 435/113; 435/115; 435/116
(58) Field of Classification Search ...................... None
See application file for complete search history.

(56) References Cited

U.S. PATENT DOCUMENTS

| 4,278,765 A | 7/1981 | Debabov et al. |
| 4,430,430 A | 2/1984 | Momose et al. |
| 4,996,147 A * | 2/1991 | Furukawa et al. ........... 435/115 |
| 5,017,483 A | 5/1991 | Furukawa et al. |
| 5,705,371 A | 1/1998 | Debabov et al. |
| 5,972,663 A | 10/1999 | Winterhalter et al. |
| 6,040,160 A | 3/2000 | Kojima et al. |
| 7,138,266 B2 | 11/2006 | Debabov et al. |
| 7,259,003 B2 | 8/2007 | Livshits et al. |
| 7,312,058 B2 | 12/2007 | Kashiwagi et al. |
| 2003/0148474 A1 | 8/2003 | Gusyatiner et al. |
| 2005/0214911 A1 | 9/2005 | Marchenko et al. |
| 2005/0239175 A1 | 10/2005 | Tabolina et al. |
| 2006/0040365 A1 | 2/2006 | Kozlov et al. |
| 2006/0088919 A1 | 4/2006 | Rybak et al. |
| 2006/0141586 A1 | 6/2006 | Rybak et al. |
| 2006/0160192 A1 | 7/2006 | Rybak et al. |
| 2006/0286643 A1 | 12/2006 | Sheremet'eva et al. |

FOREIGN PATENT DOCUMENTS

| AU | 199719218 B2 | 12/1996 |
| EP | 643135 A1 * | 3/1995 |
| EP | 1 016 710 A2 | 12/1999 |
| EP | 0 994 190 A2 | 4/2000 |
| EP | 1 013 765 | 6/2000 |
| EP | 1 013 765 A1 | 6/2000 |
| EP | 1 016 710 | 7/2000 |
| EP | 1 085 087 | 3/2001 |
| EP | 1 085 087 | 3/2002 |

OTHER PUBLICATIONS

Haynes et al., Electrophoresis, 19:1862-1871, 1998.*
Skolnick et al. Trends in Biotech., 18:34-39, 2000.*
Voet et al., Biochemistry, 2nd ed., John Wiley and Sons, Inc, 1995, p. 124.*
McGuinness et al. Lancet 337: 514-517, Mar. 1991.*
European Search Report for EP Application No. 04028876.3, dated Mar. 10, 2005.
Database UniProt 'Online! May 1, 1992, XP002318622.
Zakataeva, N.P., et al., "The novel transmembrane *Escherichia coli* proteins involved in the amino acid efflux," FEBS Letters 1999; 452:228-232.
Krämer, R., "Genetic and physiological approaches for the production of amino acids," J Biotechnol 1996; 45:1-21.
Database EMBL, Jan. 29, 1997.
European Search Report for EP Application No. 04028877.1, dated Mar. 4, 2005.
Horng, G., et al., "Simplifying Nested Radicals and Solving Polynomials by Radicals in Minimum Depth," Proceedings 31st Annual Symposium on Foundations of Computer Science, vol. II, Oct. 22-24, 1990; St. Louis, MO, IEEE Computer Society Press, Loa Alamitos, CA, pp. 847-856.
U.S. Appl. No. 10/073,293, filed Feb. 13, 2002, Tabolina et al.
U.S. Appl. No. 10/299,799, filed Nov. 20, 2002, Gusyatiner et al.
Zakataeva, et al., "The novel transmembrane *Escherichia coli* proteins involved in the amino acid efflux" FEBS Letters, Elsevier Science Publishers, Amsterdam, NL, vol. 452, Jun. 11, 1999, pp. 228-232, XP002135075.
Aleshin, et al., "A new family of amino-acid-efflux proteins" TIBS Trends in Biochemical Sciences, Elsevier Publication, Cambridge, EN, vol. 24, No. 4, Apr. 1, 1999, pp. 133-135, XP004214249.
Database EMBL Online! Jan. 29, 1997, Database accession No. AE000353, XP002219992, protein P76630, ygaz *abstract*.

(Continued)

*Primary Examiner*—Robert B Mondesi
*Assistant Examiner*—Brian J Gangle
(74) *Attorney, Agent, or Firm*—Shelly Guest Cermak; Cermak Kenealy & Vaidya LLP

(57) ABSTRACT

There is provided a method for producing L-threonine, L-valine, L-proline, L-leucine, L-methionine and L-arginine using bacterium belonging to the genus *Escherichia* wherein L-amino acid productivity of the bacterium is enhanced by enhancing an activity of proteins coded by b2682 and b2683 genes, or protein coded by b1242 or b3434 gene.

16 Claims, 1 Drawing Sheet

OTHER PUBLICATIONS

Database EMBL 'Online! Jan. 29, 1997 Database accession No. AE000353, XP002219993 protein P43667, ygah *abstract*.
Database EMBL 'Online! Feb. 1, 1997 Database accession No. D90852 XP002219994, protein P25743, yche *abstract*.
Database EMBL 'Online! Jan. 29, 1997, Database accession No. AE000420, XP002219995 protein P46851, yhgn *abstract*.
Kramer R., "Genetic and physiological approaches for the production of amino acids", Journal of Biotechnology Elsevier Science Publishers, Amsterdam, NL, vol. 45, No. 1, Feb. 12, 1996, pp. 1-21 XP004036833 ISSN: 0168-1656.
Blattner, et al., "The Complete Genome Sequence of *Escherichia coli* K-12", Science, vol. 277, Sep. 5, 1977, pp. 1453-1462, w/seq. listing, 6 pp.l.
DataBase DDBJ/EMBL/GenBank[online], Accession No. P76630, <http: //www.ncbi.nim.nih.gov/entrez/viwer.fcgi?31 23142:OLDID:5252163>, published on Feb. 1, 1998, retrieved on Aug. 13, 2007.
DataBase DDBJ/EMBL/GenBank[online], Accession No. D65048, <http://www.ncbi.nlm.nih.gov/entrez/viwer.fcgi?74 66541:OLD05:65295>, published on Oct. 8, 1999, retrieved on Aug. 13, 2007.
Lomovskaya, O., et al., "EmrR Is a Negative Regulator of the *Escherichia coli* Multidrug Resistance Pump EmrAB," J. Bacteriol. 1995;177(9):2328-2334.
Copy of Notice Of Reason for Rejection for Japanese Patent App. No. 2002-034760 (Aug. 21, 2007), with English translation thereof.
U.S. Appl. No. 60/644,562, filed Jan. 19, 2005, Rybak et al.
U.S. Appl. No. 60/673,807, filed Apr. 22, 2005, Rybak et al.
U.S. Appl. No. 60/693,507, filed Jun. 24, 2005, Rybak et al.
U.S. Appl. No. 60/693,509, filed Jun. 24, 2005, Sheremet'eva et al.
U.S. Appl. No. 60/703,426, filed Jul. 29, 2005, Rybak et al.
U.S. Appl. No. 60/703,444, filed Jul. 29, 2005, Rybak et al.
U.S. Appl. No. 60/714,943, filed Sep. 8, 2005, Filippov et al.
U.S. Appl. No. 60/714,844, filed Sep. 8, 2005, Filippov et al.
U.S. Appl. No. 60/714,848, filed Sep. 8, 2005, Filippov et al.
U.S. Appl. No. 60/714,849, filed Sep. 8, 2005, Filippov et al.
U.S. Appl. No. 60/723,566, filed Oct. 5, 2005, Rybak et al.
U.S. Appl. No. 60/723,923, filed Oct. 6, 2005, Filippov et al.
U.S. Appl. No. 60/723,925, filed Oct. 6, 2005, Rybak et al.
U.S. Appl. No. 60/723928, filed Oct. 6, 2005, Rybak et al.
U.S. Appl. No. 60/723,929, filed Oct. 6, 2005, Filippov et al.
U.S. Appl. No. 60/735,830, filed Nov. 16, 2005, Filipov et al.
U.S. Appl. No. 60/743,222, filed Feb. 3, 2006, Rybak et al.
U.S. Appl. No. 60/743,223, filed Feb. 3, 2006, Rybak et al.
U.S. Appl. No. 60/743,226, filed Feb. 3, 2006, Rybak et al.
U.S. Appl. No. 60/743,257, filed Feb. 9, 2006, Rybak et al.
U.S. Appl. No. 60/743,258, filed Feb. 9, 2006, Rybak et al.
U.S. Appl. No. 60/806,819, filed Jul. 10, 2006, Rybak et al.
U.S. Appl. No. 60/807,842, filed Jul. 20, 2006, Filippov et al.
U.S. Appl. No. 60/807,843, filed Jul. 20, 2006, Filippov et al.
U.S. Appl. No. 60/807,845, filed Jul. 20, 2006, Filippov et al.
U.S. Appl. No. 60/829,697, filed Oct. 17, 2006, Rybak et al.
U.S. Appl. No. 60/829,706, filed Oct. 17, 2006, Filippov et al.
U.S. Appl. No. 60/829,923, filed Oct. 18, 2006, Filippov et al.
U.S. Appl. No. 60/829,926, filed Oct. 18, 2006, Rybak et al.
U.S. Appl. No. 60/829,926, filed Nov. 24, 2006, Rybak et al.
U.S. Appl. No. 60/894,996, filed Mar. 15, 2007, Rybak et al.
U.S. Appl. No. 11/761,465, filed Jun. 12, 2007, Liyshits et al.
U.S. Appl. No. 11/830,961, filed Jul. 31, 2007, Filippov et al.
U.S. Appl. No. 11/830,974, filed Jul. 31, 2007, Filippov et al.
U.S. Appl. No. 60/954,663, filed Aug. 8, 2007, Filippov et al..
U.S. Appl. No. 60/954,668, filed Aug. 8, 2007, Filippov et al.
U.S. Appl. No. 60/955,968, filed Aug. 15, 2007, Filippov et al.
U.S. Appl. No. 60/956,945, filed Aug. 21, 2007, Filippov et al.
U.S. Appl. No. 11/849,403, filed Sep. 4, 2007, Rybak et al.
U.S. Appl. No. 11/849,415, filed Sep. 4, 2007, Filippov et al.
U.S. Appl. No. 60/972,028, filed Sep. 13, 2007, Filippov et al.
U.S. Appl. No. 11/934,890, filed Nov. 5, 2007, Filippov et al.
U.S. Appl. No. 11/952,297, filed Dec. 7, 2007, Rybak et al.
U.S. Appl. No. 12/173,379, filed Jan. 22, 2008, Rybak et al.
U.S. Appl. No. 12/022,299, filed Jan. 30, 2008, Rybak et al.
U.S. Appl. No. 61/031,834, filed Feb. 27, 2008, Samsonov et al.
U.S. Appl. No. 12/120,404, filed May 14, 2008, Tabolina et al.
U.S. Appl. No. 12/120,409, filed May 14, 2008, Tabolina et al.
DataBase DDBJ/EMBL/GenBank[online], Accession No. P76630, <http://www.ncbi.nlm.nih.gov/entrez/viwer.fcgi?31 23142:OLDID:5252163>, published on Feb. 1, 1998, retrieved on Aug. 13, 2007.
DataBase DDBJ/EMBL/GenBank[online], Accession No. D65048, <http://www.ncbi.nlm.nih.gov/entrez/viwer.fcgi?74 66541:OLD05:65295>, published on Oct. 8, 1999, retrieved on Aug. 13, 2007.
Lomovskaya, O., et al., "EmrR Is a Negative Regulator of the *Escherichia coli* Multidrug Resistance Pump EmrAB," J. Bacteriol. 1995; 177(9):2328-2334.
Notice of Reason for Rejection for Japanese Patent App. No. 2002-034760 (Aug. 21, 2007), with English translation thereof.
Notice of Reason for Rejection issue in Japanese Patent App. No. 2007-273972 (Jun. 10, 2008) with English translation.
Database DDBJ/EMBL/GenBank [online], Accession No. AAA58232, http://www.ncbi.nlm.nih.gov/entrez/viewer.fcgi?6063969:NCBI:1571702 published on Aug. 18, 1999, retrieved on May 29, 2008.

* cited by examiner

SEQUENCE LISTING

<160> NUMBER OF SEQ ID NOS: 16

<210> SEQ ID NO 1
<211> LENGTH: 26
<212> TYPE: DNA
<213> ORGANISM: Artificial Sequence
<220> FEATURE:
<223> OTHER INFORMATION: Synthetic DNA

<400> SEQUENCE: 1
ggtctagaca atcgttaagc gtacac                                        26

<210> SEQ ID NO 2
<211> LENGTH: 26
<212> TYPE: DNA
<213> ORGANISM: Artificial Sequence
<220> FEATURE:
<223> OTHER INFORMATION: Synthetic DNA

<400> SEQUENCE: 2
ccggatccga tatagtaacg acagtg                                        26

<210> SEQ ID NO 3
<211> LENGTH: 738
<212> TYPE: DNA
<213> ORGANISM: Escherichia coli
<220> FEATURE:
<221> NAME/KEY: CDS
<222> LOCATION: (1)..(735)
<223> OTHER INFORMATION:

<400> SEQUENCE: 3

```
atg gaa agc cct act cca cag cct gct cct ggt tcg gcg acc ttc atg      48
Met Glu Ser Pro Thr Pro Gln Pro Ala Pro Gly Ser Ala Thr Phe Met
1               5                   10                  15 gaa gga tgc aaa gac agt tta ccg att gtt att agt tat att ccg gtg      96
Glu Gly Cys Lys Asp Ser Leu Pro Ile Val Ile Ser Tyr Ile Pro Val
            20                  25                  30 gcc ttt gcg ttc ggt ctg aat gcg acc cgt ctg gga ttc tct cct ctc     144
Ala Phe Ala Phe Gly Leu Asn Ala Thr Arg Leu Gly Phe Ser Pro Leu
        35                  40                  45 gaa agc gtt ttt ttc tcc tgc atc att tat gca ggc gcg agc cag ttc     192
Glu Ser Val Phe Phe Ser Cys Ile Ile Tyr Ala Gly Ala Ser Gln Phe
    50                  55                  60 gtc att acc gcg atg ctg gca gcc ggg agt agt ttg tgg att gct gca     240
Val Ile Thr Ala Met Leu Ala Ala Gly Ser Ser Leu Trp Ile Ala Ala
65                  70                  75                  80 ctg acc gtc atg gca atg gat gtt cgc cat gtg ttg tat ggc ccg tca     288
Leu Thr Val Met Ala Met Asp Val Arg His Val Leu Tyr Gly Pro Ser
                85                  90                  95 ctg cgt agc cgt att att cag cgt ctg caa aaa tcg aaa acc gcc ctg     336
Leu Arg Ser Arg Ile Ile Gln Arg Leu Gln Lys Ser Lys Thr Ala Leu
            100                 105                 110 tgg gcg ttt ggc ctg acg gat gag gtt ttt gcc gcc gca acc gca aaa     384
Trp Ala Phe Gly Leu Thr Asp Glu Val Phe Ala Ala Ala Thr Ala Lys
        115                 120                 125 ctg gta cgc aat aat cgc cgc tgg agc gag aac tgg atg atc ggc att     432
Leu Val Arg Asn Asn Arg Arg Trp Ser Glu Asn Trp Met Ile Gly Ile
    130                 135                 140 gcc ttc agt tca tgg tca tcg tgg gta ttt ggt acg gta ata ggg gca     480
Ala Phe Ser Ser Trp Ser Ser Trp Val Phe Gly Thr Val Ile Gly Ala
145                 150                 155                 160
```

```
ttc tcc ggc agc ggc ttg ctg caa ggt tat ccc gcc gtt gaa gct gca      528
Phe Ser Gly Ser Gly Leu Leu Gln Gly Tyr Pro Ala Val Glu Ala Ala
            165                 170                 175 tta ggt ttt atg ctt ccg gca ctc ttt atg agt ttc ctg ctc gcc tct      576
Leu Gly Phe Met Leu Pro Ala Leu Phe Met Ser Phe Leu Leu Ala Ser
        180                 185                 190 ttc cag cgc aaa caa tct ctt tgc gtt acc gca gcg tta gtt ggt gcc      624
Phe Gln Arg Lys Gln Ser Leu Cys Val Thr Ala Ala Leu Val Gly Ala
    195                 200                 205 ctt gca ggc gta acg cta ttt tct att ccc gtc gcc att ctg gca ggc      672
Leu Ala Gly Val Thr Leu Phe Ser Ile Pro Val Ala Ile Leu Ala Gly
210                 215                 220 att gtc tgt ggc tgc ctc act gcg tta atc cag gca ttc tgg caa gga      720
Ile Val Cys Gly Cys Leu Thr Ala Leu Ile Gln Ala Phe Trp Gln Gly
225                 230                 235                 240 gcg ccc gat gag cta tga                                              738
Ala Pro Asp Glu Leu
                245

<210> SEQ ID NO 4
<211> LENGTH: 245
<212> TYPE: PRT
<213> ORGANISM: Escherichia coli

<400> SEQUENCE: 4

Met Glu Ser Pro Thr Pro Gln Pro Ala Pro Gly Ser Ala Thr Phe Met
1               5                   10                  15

Glu Gly Cys Lys Asp Ser Leu Pro Ile Val Ile Ser Tyr Ile Pro Val
            20                  25                  30

Ala Phe Ala Phe Gly Leu Asn Ala Thr Arg Leu Gly Phe Ser Pro Leu
        35                  40                  45

Glu Ser Val Phe Phe Ser Cys Ile Ile Tyr Ala Gly Ala Ser Gln Phe
    50                  55                  60

Val Ile Thr Ala Met Leu Ala Ala Gly Ser Ser Leu Trp Ile Ala Ala
65                  70                  75                  80

Leu Thr Val Met Ala Met Asp Val Arg His Val Leu Tyr Gly Pro Ser
                85                  90                  95

Leu Arg Ser Arg Ile Ile Gln Arg Leu Gln Lys Ser Lys Thr Ala Leu
            100                 105                 110

Trp Ala Phe Gly Leu Thr Asp Glu Val Phe Ala Ala Thr Ala Lys
        115                 120                 125

Leu Val Arg Asn Asn Arg Arg Trp Ser Glu Asn Trp Met Ile Gly Ile
    130                 135                 140

Ala Phe Ser Ser Trp Ser Ser Trp Val Phe Gly Thr Val Ile Gly Ala
145                 150                 155                 160

Phe Ser Gly Ser Gly Leu Leu Gln Gly Tyr Pro Ala Val Glu Ala Ala
                165                 170                 175

Leu Gly Phe Met Leu Pro Ala Leu Phe Met Ser Phe Leu Leu Ala Ser
            180                 185                 190

Phe Gln Arg Lys Gln Ser Leu Cys Val Thr Ala Ala Leu Val Gly Ala
        195                 200                 205

Leu Ala Gly Val Thr Leu Phe Ser Ile Pro Val Ala Ile Leu Ala Gly
    210                 215                 220

Ile Val Cys Gly Cys Leu Thr Ala Leu Ile Gln Ala Phe Trp Gln Gly
225                 230                 235                 240

Ala Pro Asp Glu Leu
```

<210> SEQ ID NO 5
<211> LENGTH: 336
<212> TYPE: DNA
<213> ORGANISM: Escherichia coli
<220> FEATURE:
<221> NAME/KEY: CDS
<222> LOCATION: (1)..(333)
<223> OTHER INFORMATION:

<400> SEQUENCE: 5

```
atg agc tat gag gtt ctg ctg ctt ggg tta cta gtt ggc gtg gcg aat     48
Met Ser Tyr Glu Val Leu Leu Leu Gly Leu Leu Val Gly Val Ala Asn
1               5                   10                  15 tat tgc ttc cgc tat ttg ccg ctg cgc ctg cgt gtg ggt aat gcc cgc     96
Tyr Cys Phe Arg Tyr Leu Pro Leu Arg Leu Arg Val Gly Asn Ala Arg
            20                  25                  30 cca acc aaa cgt ggc gcg gta ggt att ttg ctc gac acc att ggc atc    144
Pro Thr Lys Arg Gly Ala Val Gly Ile Leu Leu Asp Thr Ile Gly Ile
        35                  40                  45 gcc tcg ata tgc gct ctg ctg gtt gtc tct acc gca cca gaa gtg atg    192
Ala Ser Ile Cys Ala Leu Leu Val Val Ser Thr Ala Pro Glu Val Met
    50                  55                  60 cac gat aca cgc cgt ttc gtg ccc acg ctg gtc ggc ttc gcg gta ctg    240
His Asp Thr Arg Arg Phe Val Pro Thr Leu Val Gly Phe Ala Val Leu
65                  70                  75                  80 ggt gcc agt ttc tat aaa aca cgc agc att atc atc cca aca ctg ctt    288
Gly Ala Ser Phe Tyr Lys Thr Arg Ser Ile Ile Ile Pro Thr Leu Leu
                85                  90                  95 agt gcg ctg gcc tat ggg ctc gcc tgg aaa gtg atg gcg att ata taa    336
Ser Ala Leu Ala Tyr Gly Leu Ala Trp Lys Val Met Ala Ile Ile
            100                 105                 110
```

<210> SEQ ID NO 6
<211> LENGTH: 111
<212> TYPE: PRT
<213> ORGANISM: Escherichia coli

<400> SEQUENCE: 6

```
Met Ser Tyr Glu Val Leu Leu Leu Gly Leu Leu Val Gly Val Ala Asn
1               5                   10                  15

Tyr Cys Phe Arg Tyr Leu Pro Leu Arg Leu Arg Val Gly Asn Ala Arg
            20                  25                  30

Pro Thr Lys Arg Gly Ala Val Gly Ile Leu Leu Asp Thr Ile Gly Ile
        35                  40                  45

Ala Ser Ile Cys Ala Leu Leu Val Val Ser Thr Ala Pro Glu Val Met
    50                  55                  60

His Asp Thr Arg Arg Phe Val Pro Thr Leu Val Gly Phe Ala Val Leu
65                  70                  75                  80

Gly Ala Ser Phe Tyr Lys Thr Arg Ser Ile Ile Ile Pro Thr Leu Leu
                85                  90                  95

Ser Ala Leu Ala Tyr Gly Leu Ala Trp Lys Val Met Ala Ile Ile
            100                 105                 110
```

<210> SEQ ID NO 7
<211> LENGTH: 37
<212> TYPE: DNA
<213> ORGANISM: Artificial Sequence
<220> FEATURE:
<223> OTHER INFORMATION: Synthetic DNA -continued
<210> SEQ ID NO 8
<211> LENGTH: 34
<212> TYPE: DNA
<213> ORGANISM: Artificial Sequence
<220> FEATURE:
<223> OTHER INFORMATION: Synthetic DNA

<400> SEQUENCE: 8
ctgtttctag atcctgtgtg aaattgttat ccgc                    34

<210> SEQ ID NO 9
<211> LENGTH: 28
<212> TYPE: DNA
<213> ORGANISM: Artificial Sequence
<220> FEATURE:
<223> OTHER INFORMATION: Synthetic DNA

<400> SEQUENCE: 9
ggtctagata tggctaacat tatccggc                           28

<210> SEQ ID NO 10
<211> LENGTH: 28
<212> TYPE: DNA
<213> ORGANISM: Artificial Sequence
<220> FEATURE:
<223> OTHER INFORMATION: Synthetic DNA

<400> SEQUENCE: 10
ccggatccaa acggagcatg gcagctcc                           28

<210> SEQ ID NO 11
<211> LENGTH: 648
<212> TYPE: DNA
<213> ORGANISM: Escherichia coli
<220> FEATURE:
<221> NAME/KEY: CDS
<222> LOCATION: (1)..(645)
<223> OTHER INFORMATION:

<400> SEQUENCE: 11

```
gtg att cag acc ttt ttt gat ttt ccc gtt tac ttc aaa ttt ttc atc        48
Val Ile Gln Thr Phe Phe Asp Phe Pro Val Tyr Phe Lys Phe Phe Ile
1               5                   10                  15 ggg tta ttt gcg ctg gtc aac ccg gta ggg att att ccc gtc ttt atc        96
Gly Leu Phe Ala Leu Val Asn Pro Val Gly Ile Ile Pro Val Phe Ile
            20                  25                  30 agc atg acc agt tat cag aca gcg gca gcg cga aac aaa act aac ctt       144
Ser Met Thr Ser Tyr Gln Thr Ala Ala Ala Arg Asn Lys Thr Asn Leu
        35                  40                  45 aca gcc aac ctg tct gtg gcc att atc ttg tgg atc tcg ctt ttt ctc       192
Thr Ala Asn Leu Ser Val Ala Ile Ile Leu Trp Ile Ser Leu Phe Leu
    50                  55                  60 ggc gac acg att cta caa ctt ttt ggt ata tca att gat tcg ttc cgt       240
Gly Asp Thr Ile Leu Gln Leu Phe Gly Ile Ser Ile Asp Ser Phe Arg
65                  70                  75                  80 atc gcc ggg ggt atc ctg gtg gtg aca ata gcg atg tcg atg atc agc       288
Ile Ala Gly Gly Ile Leu Val Val Thr Ile Ala Met Ser Met Ile Ser
                85                  90                  95 ggc aag ctt ggc gag gat aaa cag aac aag caa gaa aaa tca gaa acc       336
Gly Lys Leu Gly Glu Asp Lys Gln Asn Lys Gln Glu Lys Ser Glu Thr
            100                 105                 110
```

```
gcg gta cgt gaa agc att ggt gtg gtg cca ctg gcg ttg ccg ttg atg     384
Ala Val Arg Glu Ser Ile Gly Val Val Pro Leu Ala Leu Pro Leu Met
        115                 120                 125 gcg ggg cca ggg gcg atc agt tct acc atc gtc tgg ggt acg cgt tat     432
Ala Gly Pro Gly Ala Ile Ser Ser Thr Ile Val Trp Gly Thr Arg Tyr
    130                 135                 140 cac agc att agc tat ctg ttt ggt ttc ttt gtg gct att gca ttg ttc     480
His Ser Ile Ser Tyr Leu Phe Gly Phe Phe Val Ala Ile Ala Leu Phe
145                 150                 155                 160 gct tta tgt tgt tgg gga ttg ttc cgc atg gca ccg tgg ctg gta cgg     528
Ala Leu Cys Cys Trp Gly Leu Phe Arg Met Ala Pro Trp Leu Val Arg
            165                 170                 175 gtt tta cgc cag acc ggc atc aac gtg att acg cgt att atg ggg cta     576
Val Leu Arg Gln Thr Gly Ile Asn Val Ile Thr Arg Ile Met Gly Leu
        180                 185                 190 ttg ctg atg gca ttg ggg att gaa ttt atc gtt act ggt att aag ggg     624
Leu Leu Met Ala Leu Gly Ile Glu Phe Ile Val Thr Gly Ile Lys Gly
    195                 200                 205 att ttc ccc ggc ctg ctt aat taa                                     648
Ile Phe Pro Gly Leu Leu Asn
    210             215

<210> SEQ ID NO 12
<211> LENGTH: 215
<212> TYPE: PRT
<213> ORGANISM: Escherichia coli

<400> SEQUENCE: 12

Val Ile Gln Thr Phe Phe Asp Phe Pro Val Tyr Phe Lys Phe Phe Ile
1               5                   10                  15

Gly Leu Phe Ala Leu Val Asn Pro Val Gly Ile Ile Pro Val Phe Ile
            20                  25                  30

Ser Met Thr Ser Tyr Gln Thr Ala Ala Arg Asn Lys Thr Asn Leu
        35                  40                  45

Thr Ala Asn Leu Ser Val Ala Ile Ile Leu Trp Ile Ser Leu Phe Leu
    50                  55                  60

Gly Asp Thr Ile Leu Gln Leu Phe Gly Ile Ser Ile Asp Ser Phe Arg
65                  70                  75                  80

Ile Ala Gly Gly Ile Leu Val Val Thr Ile Ala Met Ser Met Ile Ser
                85                  90                  95

Gly Lys Leu Gly Glu Asp Lys Gln Asn Lys Gln Glu Lys Ser Glu Thr
            100                 105                 110

Ala Val Arg Glu Ser Ile Gly Val Val Pro Leu Ala Leu Pro Leu Met
        115                 120                 125

Ala Gly Pro Gly Ala Ile Ser Ser Thr Ile Val Trp Gly Thr Arg Tyr
    130                 135                 140

His Ser Ile Ser Tyr Leu Phe Gly Phe Phe Val Ala Ile Ala Leu Phe
145                 150                 155                 160

Ala Leu Cys Cys Trp Gly Leu Phe Arg Met Ala Pro Trp Leu Val Arg
            165                 170                 175

Val Leu Arg Gln Thr Gly Ile Asn Val Ile Thr Arg Ile Met Gly Leu
        180                 185                 190

Leu Leu Met Ala Leu Gly Ile Glu Phe Ile Val Thr Gly Ile Lys Gly
    195                 200                 205

Ile Phe Pro Gly Leu Leu Asn
    210             215
```

<210> SEQ ID NO 13
<211> LENGTH: 28
<212> TYPE: DNA
<213> ORGANISM: Artificial Sequence
<220> FEATURE:
<223> OTHER INFORMATION: Synthetic DNA

<400> SEQUENCE: 13
ggtctagagt ccgcggcaat tatcaggg                                    28

<210> SEQ ID NO 14
<211> LENGTH: 29
<212> TYPE: DNA
<213> ORGANISM: Artificial Sequence
<220> FEATURE:
<223> OTHER INFORMATION: Synthetic DNA

<400> SEQUENCE: 14
ccagatctgg tagttgtgac gctaccggg                                   29

<210> SEQ ID NO 15
<211> LENGTH: 594
<212> TYPE: DNA
<213> ORGANISM: Escherichia coli
<220> FEATURE:
<221> NAME/KEY: CDS
<222> LOCATION: (1)..(591)
<223> OTHER INFORMATION:

<400> SEQUENCE: 15

| | | | | | | | | | | | | | | | |
|---|---|---|---|---|---|---|---|---|---|---|---|---|---|---|---|
| atg | aat | gaa | atc | att | tct | gca | gca | gtt | tta | ttg | atc | ctg | att | atg gat | 48 |
| Met | Asn | Glu | Ile | Ile | Ser | Ala | Ala | Val | Leu | Leu | Ile | Leu | Ile | Met Asp | |
| 1 | | | | 5 | | | | | 10 | | | | | 15 | |

| | | | | | | | | | | | | | | | |
|---|---|---|---|---|---|---|---|---|---|---|---|---|---|---|---|
| ccg | ctc | gga | aac | cta | cct | att | ttc | atg | tcc | gta | ctg | aaa | cat | act gaa | 96 |
| Pro | Leu | Gly | Asn | Leu | Pro | Ile | Phe | Met | Ser | Val | Leu | Lys | His | Thr Glu | |
| | | | 20 | | | | | 25 | | | | | 30 | | |

| | | | | | | | | | | | | | | | |
|---|---|---|---|---|---|---|---|---|---|---|---|---|---|---|---|
| ccg | aaa | aga | cgg | cgg | gca | atc | atg | gtg | cga | gag | ttg | ctt | att | gct ctc | 144 |
| Pro | Lys | Arg | Arg | Arg | Ala | Ile | Met | Val | Arg | Glu | Leu | Leu | Ile | Ala Leu | |
| | 35 | | | | | 40 | | | | | 45 | | | | |

| | | | | | | | | | | | | | | | |
|---|---|---|---|---|---|---|---|---|---|---|---|---|---|---|---|
| ctg | gtg | atg | ctg | gtg | ttc | ctg | ttt | gcg | ggt | gag | aaa | att | ctg | gca ttt | 192 |
| Leu | Val | Met | Leu | Val | Phe | Leu | Phe | Ala | Gly | Glu | Lys | Ile | Leu | Ala Phe | |
| 50 | | | | | 55 | | | | | 60 | | | | | |

| | | | | | | | | | | | | | | | |
|---|---|---|---|---|---|---|---|---|---|---|---|---|---|---|---|
| ctt | agc | cta | cga | gca | gaa | acc | gtc | tcc | att | tct | ggc | ggc | atc | att ctg | 240 |
| Leu | Ser | Leu | Arg | Ala | Glu | Thr | Val | Ser | Ile | Ser | Gly | Gly | Ile | Ile Leu | |
| 65 | | | | | 70 | | | | | 75 | | | | | 80 |

| | | | | | | | | | | | | | | | |
|---|---|---|---|---|---|---|---|---|---|---|---|---|---|---|---|
| ttt | ctg | atc | gcc | att | aaa | atg | att | ttc | ccc | agc | gct | tca | gga | aat agc | 288 |
| Phe | Leu | Ile | Ala | Ile | Lys | Met | Ile | Phe | Pro | Ser | Ala | Ser | Gly | Asn Ser | |
| | | | | 85 | | | | | 90 | | | | | 95 | |

| | | | | | | | | | | | | | | | |
|---|---|---|---|---|---|---|---|---|---|---|---|---|---|---|---|
| agc | ggg | ctt | ccg | gca | ggt | gaa | gag | cca | ttt | atc | gtg | ccg | ttg | gca att | 336 |
| Ser | Gly | Leu | Pro | Ala | Gly | Glu | Glu | Pro | Phe | Ile | Val | Pro | Leu | Ala Ile | |
| | | | 100 | | | | | 105 | | | | | 110 | | |

| | | | | | | | | | | | | | | | |
|---|---|---|---|---|---|---|---|---|---|---|---|---|---|---|---|
| ccg | tta | gtc | gcc | ggg | ccg | act | att | ctc | gcc | acg | ctg | atg | ttg | ttg tct | 384 |
| Pro | Leu | Val | Ala | Gly | Pro | Thr | Ile | Leu | Ala | Thr | Leu | Met | Leu | Leu Ser | |
| | 115 | | | | | 120 | | | | | 125 | | | | |

| | | | | | | | | | | | | | | | |
|---|---|---|---|---|---|---|---|---|---|---|---|---|---|---|---|
| cat | cag | tac | ccg | aat | cag | atg | ggg | cat | ctg | gtg | att | gct | ctg | ctg ctg | 432 |
| His | Gln | Tyr | Pro | Asn | Gln | Met | Gly | His | Leu | Val | Ile | Ala | Leu | Leu Leu | |
| 130 | | | | | 135 | | | | | 140 | | | | | |

| | | | | | | | | | | | | | | | |
|---|---|---|---|---|---|---|---|---|---|---|---|---|---|---|---|
| gcc | tgg | ggc | ggc | acc | ttt | gtc | atc | ctg | cta | cag | tct | tcg | cta | ttt tta | 480 |
| Ala | Trp | Gly | Gly | Thr | Phe | Val | Ile | Leu | Leu | Gln | Ser | Ser | Leu | Phe Leu | |
| 145 | | | | | 150 | | | | | 155 | | | | | 160 |

| | | | | | | | | | | | | | | | |
|---|---|---|---|---|---|---|---|---|---|---|---|---|---|---|---|
| cgt | ctg | ctg | ggc | gag | aaa | ggg | gtg | aac | gca | ctt | gaa | cgc | ctg | atg gga | 528 |
| Arg | Leu | Leu | Gly | Glu | Lys | Gly | Val | Asn | Ala | Leu | Glu | Arg | Leu | Met Gly | |
| | | | | 165 | | | | | 170 | | | | | 175 | |

```
-continued ttg att ctg gtg atg atg gca acc cag atg ttc ctc gac ggc att cga    576
Leu Ile Leu Val Met Met Ala Thr Gln Met Phe Leu Asp Gly Ile Arg
            180                 185                 190 atg tgg atg aag ggg taa                                            594
Met Trp Met Lys Gly
        195

<210> SEQ ID NO 16
<211> LENGTH: 197
<212> TYPE: PRT
<213> ORGANISM: Escherichia coli

<400> SEQUENCE: 16

Met Asn Glu Ile Ile Ser Ala Ala Val Leu Leu Ile Leu Ile Met Asp
1               5                   10                  15

Pro Leu Gly Asn Leu Pro Ile Phe Met Ser Val Leu Lys His Thr Glu
            20                  25                  30

Pro Lys Arg Arg Arg Ala Ile Met Val Arg Glu Leu Leu Ile Ala Leu
        35                  40                  45

Leu Val Met Leu Val Phe Leu Phe Ala Gly Glu Lys Ile Leu Ala Phe
    50                  55                  60

Leu Ser Leu Arg Ala Glu Thr Val Ser Ile Ser Gly Gly Ile Ile Leu
65                  70                  75                  80

Phe Leu Ile Ala Ile Lys Met Ile Phe Pro Ser Ala Ser Gly Asn Ser
                85                  90                  95

Ser Gly Leu Pro Ala Gly Glu Glu Pro Phe Ile Val Pro Leu Ala Ile
            100                 105                 110

Pro Leu Val Ala Gly Pro Thr Ile Leu Ala Thr Leu Met Leu Leu Ser
        115                 120                 125

His Gln Tyr Pro Asn Gln Met Gly His Leu Val Ile Ala Leu Leu Leu
    130                 135                 140

Ala Trp Gly Gly Thr Phe Val Ile Leu Leu Gln Ser Ser Leu Phe Leu
145                 150                 155                 160

Arg Leu Leu Gly Glu Lys Gly Val Asn Ala Leu Glu Arg Leu Met Gly
                165                 170                 175

Leu Ile Leu Val Met Met Ala Thr Gln Met Phe Leu Asp Gly Ile Arg
            180                 185                 190

Met Trp Met Lys Gly
        195
```

METHOD FOR PRODUCING L-AMINO ACID USING BACTERIA BELONGING TO THE GENUS ESCHERICHIA

TECHNICAL FIELD

The present invention relates to biotechnology, specifically to a method for producing L-amino acids by fermentation and more specifically to genes derived from bacteria *Escherichia coli*. The genes are useful for improvement of L-amino acid productivity, for example, L-threonine, L-valine, L-proline, L-leucine, L-methionine and L-arginine.

BACKGROUND ART

Conventionally the L-amino acids have been industrially produced by method of fermentation utilizing strains of microorganisms obtained from natural sources or mutant of the same especially modified to enhance L-amino acid productivity.

There have been disclosed many techniques to enhance L-amino acid productivity, for example, by transformation of microorganism by recombinant DNA (see, for example, U.S. Pat. No. 4,278,765). These techniques based on the increasing of activities of the enzymes involved into amino acid biosynthesis and/or desensitizing the target enzymes to the feedback inhibition by produced L-amino acid (see, for example, Japanese Laid-open application No 56-18596 (1981), WO 95/16042 or U.S. Pat. Nos. 5,661,012 and 6,040,160).

On the other hand, increased L-amino acid excretion can enhance the productivity of strain producing L-amino acid. Strain of bacterium belonging to the genus *Corynebacterium* having increased expression of L-lysine excretion gene (lysE gene) is disclosed (WO 9723597A2). In addition, genes coding for the efflux proteins suitable for secretion of L-cysteine, L-cystine, N-acetylserine or thiazolidine derivatives are also disclosed (U.S. Pat. No. 5,972,663).

At present several *Eseherichia coli* genes coding for putative membrane proteins enhancing L-amino acid production are disclosed. Additional copy of rhtB gene makes a bacterium more resistant to L-homoserine and enhances production of L-homoserine, L-threonine, L-aianine, L-valine and L-isoleucinc (European patent application EP994 1 90A2). Additional copy of rhtC gene makes a bacterium more resistant to L-homoserine and L-threonine and enhances production of L-homoserine, L-threonine and L-leucine (European patent application EP1013765A1). Additional copy of yahN yeaS, yfiK and yggA genes enhance production of L-glutamic acid, L-lysine, L-threonine L-alanine, L-histidine, Lproline, L-arginine, L-valine and L-isoleucine (European patent application EP1016710A2). And though complete genome sequence of *Eseheriehia coli* strain K-12 is described (Blattner F. R., Plunkeft G., Bloch C. A. et al., Science, 227, 1453-1474, 1997;there are many OREs, the function of which still remains unknown.

DISCLOSURE OF THE INVENTION

An object of present invention is to enhance the productivity of L-amino acid producing strains and to provide a method for producing L-amino acid, for example, L-threonine, L-valine, L-proline, L-leucine or L-methionine or L-arginine, using the strains.

This aim was achieved by identifying genes coding for proteins, which are not involved into biosynthetic pathway of target L-amino acid but enhance its production. An example of such protein could be a membrane protein having L-amino acid excretion activity. Based on the analysis of complete genome sequence of *Escherichia coli*, proteins with 4 or more putative transmembrane segments (TMS) were selected. As a result of diligent screening, the present inventors have identified several genes among them, that is, b2682, b2683, b1242 and b3434, and thoroughly studied it. The genes b2682 and b2683 have been known as putative CDS which may encode functionally unknown proteins (nucleotide numbers 92 to 829 and 819 to 1154 in the sequence of GenBank accession AE000353 U00096, respectively). The gene b2683 is also known as ygaH. The gene b1242 has been known as putative CDS which may encode functionally unknown protein (numbers 8432 to 9079 in the sequence of GenBank accession AE000222 U00096). The gene b1242 is also known as ychE. The gene b3434 also has been known as putative CDS which may encode functionally unknown protein (numbers 1463 to 2056 in the sequence of GenBank accession AE000420 U00096). The gene b3434 is also known as yhgN.

Also the present inventors have found that by enhancing the activity of the protein encoded by b2682, b2683, b1242 or b3434 gene the productivity of L-amino acid producing strain is enhanced. Thus the present invention has been completed.

The present inventions are as follows:

1). An L-amino acid producing bacterium belonging to the genus *Escherichia*, wherein the bacterium has been modified so that the L-amino acid production by the bacterium should be enhanced by enhancing activities of proteins as defined in the following (A) or (B), and (C) or (D) in a cell of the bacterium:

(A) a protein which comprises the amino acid sequence shown in SEQ ID NO:3 in Sequence listing;

(B) a protein which comprises an amino acid sequence including deletion, substitution, insertion or addition of one or several amino acids in the amino acid sequence shown in SEQ ID NO:3 in Sequence listing, and which has an activity of making bacterium having enhanced resistance to the L-amino acids and/or its analogs;

(C) a protein which comprises the amino acid sequence shown in SEQ ID NO:5 in Sequence listing;

(D) a protein which comprises an amino acid sequence including deletion, substitution, insertion or addition of one or several amino acids in the amino acid sequence shown in SEQ ID NO: 5 in Sequence listing, and which has an activity of making bacterium having enhanced resistance to the L-amino acids and/or its analogs.

(hereinafter, the proteins as defined in the above (A) or (B) and (C) or (D) are referred to as "proteins of the first embodiment of the present invention" and the bacterium belonging to the genus *Escherichia* which is enhanced the activities of the above proteins is sometimes referred to as "a bacterium of the first embodiment of the present invention)

2). The bacterium according to the above bacterium, wherein the activities of the proteins as defined in (A) or (B) and (C) or (D) are enhanced by transformation of the bacterium with a DNA coding for the proteins as defined in (A) or (B) and (C) or (D), or by alteration of expression regulation sequence of the DNA on the chromosome of the bacterium.

3). The bacterium according to the above bacterium, wherein the transformation is performed with a multicopy vector.

4). A method for producing L-amino acid, which comprises cultivating the bacterium according to the above bacterium in a culture medium and collecting from the culture medium L-amino acid to be produced and accumulated.

5) The method according to the above method, wherein L-amino acid is L-threonine.

6) The method according to the above method, wherein the bacterium has been modified so that the bacterium should have enhanced expression of threonine operon.

7) The method according to the above method, wherein L-amino acid is L-valine.

8) The method according to the above method, wherein the bacterium has been modified so that the bacterium should have enhanced expression of ilv operon.

9) The method according to the above method, wherein L-amino acid is L-proline.

10) The method according to the above method, wherein the bacterium has been modified so that the bacterium should have enhanced expression of genes for proline biosynthesis.

11) The method according to the above method, wherein L-amino acid is L-leucine.

12) The method according to the above method, wherein the bacterium has been modified so that the bacterium should have enhanced expression of leu operon.

13) The method according to the above method, wherein L-amino acid is L-methionine.

14) The method according to the above method, wherein the bacterium has been modified so that the bacterium should have enhanced expression of met regulon.

15) An L-amino acid producing bacterium belonging to the genus *Escherichia*, wherein the bacterium has been modified so that the L-amino acid production by the bacterium should be enhanced by enhancing activities of proteins as defined in the following (E) or (F) in a cell of the bacterium:

(E) a protein which comprises the amino acid sequence shown in SEQ ID NO:11 in Sequence listing;

(F) a protein which comprises an amino acid sequence including deletion, substitution, insertion or addition of one or several amino acids in the amino acid sequence shown in SEQ ID NO:11 in Sequence listing, and which has an activity of making bacterium having enhanced resistance to the L-amino acids and/or its analogs;

(hereinafter, the proteins as defined in the above (E) or (F) are sometimes referred to as "proteins of the second embodiment of the present invention" and the bacterium belonging to the genus *Escherichia* which is enhanced the activities of the proteins (E) or (F) is sometimes referred to as "a bacterium of the second embodiment of the present invention")

16) The bacterium according to the above bacterium, wherein the activities of the proteins as defined in (E) or (F) are enhanced by transformation of the bacterium with a DNA coding for the proteins as defined in (E) or (F), or by alteration of expression regulation sequence of the DNA on the chromosome of the bacterium.

17) The bacterium according to the above bacterium, wherein the transformation is performed with a multicopy vector.

18) A method for producing L-amino acid, which comprises cultivating the bacterium according to the above bacterium in a culture medium and collecting from the culture medium L-amino acid to be produced and accumulated.

19) The method according to the above method, wherein L-amino acid is L-threonine.

20) The method according to the above method, wherein the bacterium has been modified so that the bacterium should have enhanced expression of threonine operon.

21) The method according to the above method, wherein L-amino acid is L-valine.

22) The method according to the above method, wherein the bacterium has been modified so that the bacterium should have enhanced expression of ilv operon.

23) An L-amino acid producing bacterium belonging to the genus *Escherichia*, wherein the bacterium has been modified so that the L-amino acid production by the bacterium should be enhanced by enhancing activities of proteins as defined in the following (G) or (H) in a cell of the bacterium:

(G) a protein which comprises the amino acid sequence shown in SEQ ID NO:15 in Sequence listing;

(H) a protein which comprises an amino acid sequence including deletion, substitution, insertion or addition of one or several amino acids in the amino acid sequence shown in SEQ ID NO:15 in Sequence listing, and which has an activity of making bacterium having enhanced resistance to the L-amino acids and/or its analogs, such as DL-o-methylserine, 6-diazo-5-oxo-L-norleucine and DL-β-hydroxy-norvaline, and having enhanced sensitivity to S-(2-aminoethyl)cysteine; (hereinafter, the proteins as defined in the above (G) or (H) are sometimes referred to as "proteins of the third embodiment of the present invention" and the bacterium belonging to the genus *Escherichia* which is enhanced the activities of the proteins (E) or (F) is sometimes referred to as "a bacterium of the third embodiment of the present invention")

24) The bacterium according to the above bacterium, wherein the activities of the proteins as defined in (G) or (H) are enhanced by transformation of the bacterium with a DNA coding for the proteins as defined in (G) or (H), or by alteration of expression regulation sequence of the DNA on the chromosome of the bacterium.

25) The bacterium according to the above bacterium, wherein the transformation is performed with a multicopy vector.

26) A method for producing L-amino acid, which comprises cultivating the bacterium according to the above bacterium in a culture medium and collecting from the culture medium L-amino acid to be produced and accumulated.

27) The method according to the above method, wherein L-amino acid is L-arginine.

28) The method according to the above method, wherein the bacterium has been modified so that the bacterium should have enhanced expression of arginine regulon.

29) The method according to the above method, wherein L-amino acid is L-proline.

30) The method according to the above method, wherein the bacterium has been modified so that the bacterium should have enhanced expression of genes for proline biosynthesis.

The method for producing L-amino acid includes production of L-threonine using L-threonine producing bacterium wherein activities of the proteins of the present invention such as that comprising amino acid sequence shown in SEQ ID NO:3 and SEQ ID NO:5 are enhanced. Also a method for producing L-amino acid includes production of L-valine using L-valine producing bacterium wherein activities of the proteins of the present invention such as that comprising amino acid sequence shown in SEQ ID NO:3 and SEQ ID NO:5 are enhanced. Besides, method for producing L-amino acid includes production of L-proline using L-proline producing bacterium wherein activities of the proteins of the present invention such as that comprising amino acid sequence shown in SEQ ID NO:3 and SEQ ID NO:5 are enhanced. Moreover, method for producing L-amino acid includes production of L-leucine using L-leucine producing bacterium wherein activities of the proteins of the present invention such as that comprising amino acid sequence shown in SEQ ID NO:3 and SEQ ID NO:5 are enhanced. And, method for producing L-amino acid includes production of L-methionine using L-methionine producing bacterium wherein activities of the proteins of the present invention such as that comprising amino acid sequence shown in SEQ ID NO:3 and SEQ ID NO:5 are enhanced.

Further, the method for producing L-amino acid includes production of L-threonine using L-threonine producing bacterium wherein activities of the proteins of the present invention such as that comprising amino acid sequence shown in SEQ ID NO:11 are enhanced. Also a method for producing L-amino acid includes production of L-valine using L-valine producing bacterium wherein activities of the proteins of the present invention such as that comprising amino acid sequence shown in SEQ ID NO:11 are enhanced.

Still further, the method for producing L-amino acid includes production of L-arginine using L-arginine producing bacterium wherein activities of the proteins of the present invention such as that comprising amino acid sequence shown in SEQ ID NO:15 are enhanced. Also, method for producing L-amino acid includes production of L-proline using L-proline producing bacterium wherein activities of the proteins of the present invention such as that comprising amino acid sequence shown in SEQ ID NO:15 are enhanced.

The present invention will be explained in detail below.

The bacterium of the present invention is an L-amino acid producing bacterium belonging to the genus *Escherichia*, wherein the bacterium has been modified so that the L-amino acid production by the bacterium should be enhanced by enhancing activities of the proteins of the present invention in a cell of the bacterium.

In the present invention, "L-amino acid producing bacterium" means a bacterium which has an ability to accumulate L-amino acid in a medium, when the bacterium is cultured in the medium. The L-amino acid producing ability may be possessed by the bacterium as a property of a wild strain of the bacterium or may be imparted or enhanced by breeding.

The bacterium of the present invention is L-amino acid producing bacterium belonging to the genus *Escherichia* having enhanced activities of proteins, which enhance the productivity of the target L-amino acid. Concretely the bacterium of present invention is L-amino acid producing bacterium belonging to the genus *Escherichia* which has enhanced activity of at least one or two of the proteins of the present invention.

The term "enhancing an activity of a protein" means that the activity per cell has become higher than that of a non-modified strain, for example, a wild-type bacterium belonging to the genus *Esherichia*. For example, there can be mentioned a case where number of the protein molecules per cell increases, a case where specific activity per the protein molecule increases and so forth. Further, as a wild-type bacterium belonging to the genus *Eshcerichia* that serves as an object for comparison, for example, the wild type strain of *Escherichia coli* can be mentioned.

Concretely the bacterium of the first embodiment of the present invention harbors the DNA which overexpresses at least one of b2682 and b2683 gene, preferably both of these genes, on chromosomal DNA or plasmid in the bacterium and has enhanced ability to produce L-amino acid, for example L-threonine, L-valine, L-proline, L-leucine or L-methionine. The bacterium of the second embodiment of the present invention harbors the DNA having overexpressed b1242 gene on chromosomal DNA or plasmid in the bacterium and has enhanced ability to produce L-amino acid, for example L-threonine and/or L-valine. The bacterium of the third embodiment of the present invention harbors the DNA having overexpressed b3434 gene on chromosomal DNA or plasmid in the bacterium and has enhanced ability to produce L-amino acid, for example, L-arginine and/or L-proline.

The proteins of the first embodiment of the present invention include ones as defined in the following (A) or (B), and (C) or (D):

(A) a protein which comprises the amino acid sequence shown in SEQ ID NO:3 in Sequence listing;

(B) a protein which comprises an amino acid sequence including deletion, substitution, insertion or addition of one or several amino acids in the amino acid sequence shown in SEQ ID NO:3 in Sequence listing, and which has an activity of making bacterium having enhanced resistance to the L-amino acids and/or its analogs;

(C) a protein which comprises the amino acid sequence shown in SEQ ID NO5 in Sequence listing;

(D) a protein which comprises an amino acid sequence including deletion, substitution, insertion or addition of one or several amino acids in the amino acid sequence shown in SEQ ID NO: 5 in Sequence listing, and which has an activity of making bacterium having enhanced resistance to the L-amino acids and/or its analogs.

The number of "several" amino acids differs depending on the position or the type of amino acid residues in the three-dimensional structure of the protein. It may be 2 to 24, preferably 2 to 12, and more preferably 2 to 5 for the protein (A), and 2 to 11, preferably 2 to 7, and more preferably 2 to 5 for the protein (C), respectively.

The proteins of the second embodiment of the present invention include ones as defined in the following (E) or (F):

(E) a protein which comprises the amino acid sequence shown in SEQ ID NO:11 in Sequence listing;

(F) a protein which comprises an amino acid sequence including deletion, substitution, insertion or addition of one or several amino acids in the amino acid sequence shown in SEQ ID NO:11 in Sequence listing, and which has an activity of making bacterium having enhanced resistance to the L-amino acids and/or its analogs;

The number of "several" amino acids differs depending on the position or the type of amino acid residues in the three-dimensional structure of the protein It may be 2 to 22, preferably 2 to 11, and more preferably 2 to 5 for the protein (E).

The proteins of the third embodiment of the present invention include ones as defined in the following (G) or (H):

(G) a protein which comprises the amino acid sequence shown in SEQ ID NO:15 in Sequence listing;

(H) a protein which comprises an amino acid sequence including deletion, substitution, insertion or addition of one or several amino acids in the amino acid sequence shown in SEQ ID NO:15 in Sequence listing, and which has an activity of making bacterium having enhanced resistance to the L-amino acids and/or its analogs, such as DL-o-methylserine, 6-diazo-5-oxo-L-norleucine and DL-β-hydroxy-norvaline, and having enhanced sensitivity to S-(2-aminoethyl)cysteine. The number of "several" amino acids differs depending on the position or the type of amino acid residues in the three-dimensional structure of the protein It may be 2 to 20, preferably 2 to 10, and more preferably 2 to 5 for the protein (G).

Enhanced resistance to L-amino acids and/or its analogs means ability for bacterium to grow on a minimal medium containing L-amino acid or its analog in concentration under which the unmodified strain or the wild type strain, or the parental strain of the bacterium cannot grow, or ability for bacterium to grow faster on a medium containing L-amino acid or its analog than the unmodified strain or the wild type strain, or the parental strain of the bacterium.

More concretely, it can be said that *E. coli* strain has enhanced resistance to the L-amino acid or its analog if the strain forms a colony which is larger than that of the unmodified strain or wild type strain of *E. coli* after 2-4 days incubation at 37° C. on a plate with solid Adams medium at 37° C. when the strain is cultivated on an agar medium containing the L-amino acid or its analog under an appropriate condition. The term "an appropriate condition" refers to temperature, pH, air supply or optional presence of essential nutrients or the like for the *E. coli* strain which is to be cultivated.

L-amino acid analogs are exemplified by 3,4-dihydroproline, DL-thiaisoleucine, DL-o-methylserine, 4-azaleucine, norleucine, L-o-fluorophenylalanine and DL-o-fluorophenylalanine, homoserine, 6-diazo-5-oxo-L-norleucine and DL-β-hydroxy-norvaline.

Above mentioned concentration of L-amino acid or its analog, under which the unmodified strain or the wild type strain of the bacterium cannot grow, varies very significantly (from 0.5 µg/ml for DL-thiaisoleucine to 9600 µg/ml for DL-o-methylserine) depending on the structure of used compound. For example, such concentration is generally 7 to 70 µg/ml, preferably 20 to 25 µg/ml in case of 3,4-dihydroproline; generally 0.5 to 5 µg/ml, preferably 0.9 to 1.1 in case of DL-thiaisoleucine; generally 1100 to 9600 µg/ml, preferably 3000 to 3500 in case of DL-o-methylserine; generally 15 to 150 µg/ml, preferably 40 to 50 µg/ml in case of 4-azaleucine; generally 150 to 1500 µg/ml, preferably 450 to 550 µg/ml in case of norleucine; generally 0.6 to 6 µg/ml, preferably 1.5 to 2 µg/ml in case of L-o-fluorophenylalanine; generally 2 to 20 µg/ml, preferably 5 to 7 µg/ml in case of DL-o-fluorophenylalanine; and generally 330 to 3300 µg/ml, preferably 900 to 1100 µg/ml in case of homoserine, generally 5 to 50 µg/ml, preferably 12 to 18 in case of 6-diazo-5-oxo-L-norleucine, and generally 25 to 250 µg/ml, preferably 70 to 90 µg/ml in case of DL-β-hydroxy-norvaline Sensitivity to L-amino acids and/or its analogs means ability for bacterium to grow in longer proliferation time than the unmodified strain or the wild type strain on a minimal medium containing a concentration of L-amino acid or its analog. Alternatively, sensitivity to L-amino acids and/or its analogs means ability for bacterium not to grow on a minimal medium containing L-amino acid or its analog in a concentration under which the unmodified strain or the wild type strain of the bacterium grow. Such L-amino acid analog is exemplified by S-(2-aminoethyl)cysteine. Above mentioned concentration is generally 0.2 to 2.0 µg/ml, preferably 0.5 to 1.0 µg/ml in case of S-(2-aminoethyl)cysteine.

The bacterium of the present invention also includes one wherein the activities of the proteins of the present invention are enhanced by transformation of the bacterium with DNA coding for protein as defined in (A) or (B), and (C) or (D), or (E) or (F), or (G) or (H), or by alteration of expression regulation sequence of the DNA on the chromosome of the bacterium.

The DNA, which is used for modification of the bacterium of the present invention, codes for putative membrane protein. Concretely the DNA codes for protein having 4 or more transmembrane segments. Such DNA may code for proteins having L-amino acid excretion activity. More concretely, the DNA is represented by b2682, b2683, b1242 and b3434 genes. It is necessary to notice that coding region of b2682 gene at position 728-738 and coding region of b2683 gene at position 1-11 are overlapping. Both genes can be obtained by, for example, PCR using primers having nucleotide sequence shown in SEQ ID No: 1 and 2 as a single PCR product. The b1242 gene can be obtained by, for example, PCR using primers having nucleotide sequence shown in SEQ ID No: 9 and 10. The b3434 gene can be obtained by, for example, PCR using primers having nucleotide sequence shown in SEQ ID No: 13 and 14.

Analysis of complete genome sequence of *Escherichia coli* allowed to select the genes coding for proteins having 4 or more putative TMS. Proteins with known function and transporters described by Paulsen I. T., Sliwinski M. I., Saier M. H. (*J. Mol. Biol.,* 1998, 277, 573) and Linton K. J., Higgins C. F. (*Molecular Microbiology,* 1998, 28(1), 5) were excluded from the group to be screened. As a result of diligent screening among the rest of genes, several genes coding for putative membrane exporters were chosen. And it was found that the overexpression of b2682 and b2683 genes, or b1242 or b3434 gene enhances the L-amino acid production by L-amino acid producing strain.

The DNA of the present invention includes a DNA coding for the protein which include deletion, substitution, insertion or addition of one or several amino acids in one or more positions on the protein (A) or (C) as long as they do not lose the activity of the protein. Although the number of "several" amino acids differs depending on the position or the type of amino acid residues in the three-dimensional structure of the protein, it may be 2 to 24, preferably 2 to 12, and more preferably 2 to 5 for the protein (A), and 2 to 11, preferably 2 to 7, and more preferably 2 to 5 for the protein (C), respectively.

Further, the DNA of the present invention includes a DNA coding for the protein which include deletion, substitution, insertion or addition of one or several amino acids in one or more positions on the protein (E) as long as they do not lose the activity of the protein. Although the number of "several" amino acids differs depending on the position or the type of amino acid residues in the three-dimensional structure of the protein, it may be 2 to 22, preferably 2 to 11, and more preferably 2 to 5 for the protein (E). Still further, the DNA of the present invention includes a DNA coding for the protein which include deletion, substitution, insertion or addition of one or several amino acids in one or more positions on the protein (G) as long as they do not lose the activity of the protein. Although the number of "several" amino acids differs depending on the position or the type of amino acid residues in the three-dimensional structure of the protein, it may be 2 to 20, preferably 2 to 10, and more preferably 2 to 5 for the protein (G).

The DNA coding for substantially the same protein as the protein defined in (A), (C), (E) or (G) may be obtained by, for example, modification of nucleotide sequence coding for the protein defined in (A), (C), (E) or (G) using site-directed mutagenesis so that one or more amino acid residue will be deleted, substituted, inserted or added. Such modified DNA can be obtained by conventional methods using treatment with reagents and conditions generating mutations. Such treatment includes treatment the DNA coding for proteins of present invention with hydroxylamine or treatment the bacterium harboring the DNA with UV irradiation or reagent such as N-methyl-N'-nitro-N-nitrosoguanidine or nitrous acid.

The DNA of the present invention include variants which can be found in the different strains and variants of bacteria belonging to the genus *Escherichia* according to natural diversity. The DNA coding for such variants can be obtained by isolating the DNA, which hybridizes with b2862, b2683, b1242, or b3434 gene or part of the genes under the stringent conditions, and which codes the protein enhancing L-amino acid production. The term "stringent conditions" referred to herein is a condition under which so-called specific hybrid is formed, and non-specific hybrid is not formed. For example, the stringent conditions includes a condition under which DNAs having high homology, for instance DNAs having homology no less than 70% to each other, are hybridized.

Alternatively, the stringent conditions are exemplified by conditions which comprise ordinary condition of washing in Southern hybridization, e.g., 60° C., 1×SSC, 0.1% SDS, preferably 0.1×SSC, 0.1% SDS. As a probe for the DNA which codes for variants and hybridizes with b2862, b2683, b1242, or b3434 gene, a partial sequence of the nucleotide sequence of SEQ ID NO: 3 or SEQ ID NO: 5 respectively can also be used. Such a probe may be prepared by PCR using oligonucleotides produced based on the nucleotide sequence of SEQ ID NO: 3, 5, 11 or 15 as primers, and a DNA fragment containing the nucleotide sequence of SEQ ID NO: 3, 5, 11 or 15 as a template. When a DNA fragment in a length of about 300 bp is used as the probe, the conditions of washing for the hybridization consist of, for example, 50° C., 2×SSC, and 0.1% SDS.

Transformation of bacterium with DNA coding for protein means introduction of the DNA into bacterium cell for example by conventional methods to increase expression of the gene coding for the protein of present invention and to enhance the activity of the protein in the bacterial cell.

Techniques for enhancement of gene expression includes methods increasing the gene copy number. Introduction of a gene into a vector that is able to function in a bacterium belonging to the genus *Escherichia* increases copy number of the gene. For such purposes multi-copy vectors can be preferably used. The multi-copy vector is exemplified by pBR322, pMW119, pUC19, pET22b or the like.

Besides, enhancement of gene expression can be achieved by introduction of multiple copies of the gene into bacterial chromosome by, for example, method of homologous recombination or the like.

In case that expression of two or more genes is enhanced, the genes may be harbored together on the same plasmid or separately on different plasmids. It is also acceptable that one of the genes is harbored on a chromosome, and the other gene is harbored on a plasmid.

On the other hand, enhancement of gene expression can be achieved by alteration of expression regulation sequence of the gene. Alteration of expression regulation sequence of a gene includes introducing mutation in the inherent expression regulation sequence of the gene such as a promoter so that the expression of the gene is enhanced (WO00/18935) and locating the DNA of the present invention under control of a potent promoter. For example, lac promoter, trp promoter, trc promoter, $P_L$ promoter of lambda phage are known as potent promoters. Using the potent promoter can be combined with multiplication of gene copies.

The bacterium of the present invention can be obtained by introduction of the aforementioned DNAs into bacterium inherently having ability to produce L-amino acid. Alternatively, the bacterium of present invention can be obtained by imparting ability to produce L-amino acid to the bacterium already harboring the DNAs. For the parent strain which is to be enhanced in activities of the proteins of the present invention, L-threonine producing bacteria belonging to the genus *Escherichia* such as strains VL2054 (VKPM B-8067), VNII-Genetika 472T23 (U.S. Pat. No. 5,631,157), VKPM B-3996 (U.S. Pat. Nos. 5,175,107 and 5,976,843), KCCM-10132 (WO009660A1), KCCM-10133 (WO009661A1) or the like can be employed. Also for the parent strain which is to be enhanced in activities of the proteins of the present invention, L-valine producing bacteria belonging to the genus *Escherichia* such as H-81 (VKPM B-8066), NRRL B-12287 and NRRL B-12288 (U.S. Pat. No. 4,391,907), VKPM B-4411 (U.S. Pat. No. 5,658,766), VKPM B-7707 (European patent application EP1016710A2) or the like is employed. Besides, for the parent strain which is to be enhanced in activities of the proteins of the present invention, L-proline producing bacteria belonging to the genus *Escherichia* such as NRRL B-12403 and NRRL B-12404 (GB2075056), VKPM B-8012 (Russian patent application 2000124295), plasmid mutants described in the patent DE3127361, plasmid mutants described by Bloom F. R. et al. (The 15$^{th}$ Miami winter symposium, 1983, p. 34) or the like are employed. Also, for the parent strain which is to be enhanced in activities of the proteins of the present invention, L-leucine producing bacteria belonging to the genus *Escherichia* such as H-9070 (FERM BP-4704) and H-9072 (FERM BP-4706) (U.S. Pat. No. 5,744,331), VKPM B-7386 and VKPM B-7388 (RU2140450), W1485atpA401/pMWdAR6, W1485lip2/pMWdAR6 and AJ12631/pMWdAR6 (EP0872547) or the like are employed. And, for the parent strain which is to be enhanced in activities of the proteins of the present invention, L-methionine producing bacteria belonging to the genus *Escherichia* such as AJ11539 (NRRL B-12399), AJ11540 (NRRL B-12400), AJ11541 (NRRL B-12401), AJ 11542 (NRRL B-12402) (GB2075055) or the like are employed as well.

Further, for the parent strain which is to be enhanced in activity of the proteins of the present invention, L-arginine producing bacteria belonging to the genus *Escherichia* such as strains AJ11531 and AJ11538 (JP56106598A2), AJ11593 (FERM P-5616) and AJ11594 (FERM P-5617) (Japanese Patent Laid-open No. 57-5693) or the like can be employed.

The bacterium of the present invention may be further enhanced expression of one or more genes which are involved in L-amino acid biosynthesis. Such genes are exemplified by threonine operon, which preferably comprises a gene encoding aspartate kinase-homoserine dehydrogenase of which feedback inhibition by L-threonine is desensitized (Japanese Patent Publication No. 1-29559), for L-threonine producing bacteria. Such genes are exemplified by ilv operon, i.e. ilvGMEDA operon, which does not preferably express threonine deaminase and of which attenuation is suppressed (Japanese Patent Laid-Open Publication No. 8-47397), for L-valine producing bacteria. Such genes are exemplified by genes for L-proline biosynthesis, which are preferably represented by gene proB encoding for glutamate kinase of which feedback inhibition by L-proline is desensitized (DE3127361), for L-proline producing bacteria. Also, such genes are exemplified by leucine operon, i.e. leu operon, which preferably comprises a gene coding for isopropylmalate synthase of which feedback inhibition by L-leucine is desensitized (Russian patent application 99114325), for L-leucine producing bacteria. Also, such genes are exemplified by methionine regulon, for L-methionine producing bacteria. The methionine regulon may have mutated genes coding for proteins lowered in activity in repressing the amino acid biosynthesis. Such gene is exemplified by variation type metJ gene coding for a L-methionine biosynthesis-relating repressor protein from *E. coli* of which activity in repressing methionine biosynthesis is lowered (JP 2000-157267 A2). Further, such gene is exemplified by arginine regulon, which preferably comprises a gene encoding N-acetylglutamate synthase of which feedback inhibition by L-arginine is desensitized (Rajagopal B. S. et al, Appl. Environ. Microbiol., 1998, v. 64, No. 5, p. 1805-1811).

The method of the present invention includes method for producing L-threonine, comprising steps of cultivating the bacterium of the first embodiment of the present invention in a culture medium, to allow L-threonine to be produced and accumulated in the culture medium, and collecting L-threonine from the culture medium. Also the method of present invention includes method for producing L-valine, comprising steps of cultivating the bacterium of the present invention in a culture medium, to allow L-valine to be produced and accumulated in the culture medium, and collecting L-valine from the culture medium. Besides, the method of present invention includes method for producing L-proline, comprising steps of cultivating the bacterium of the present invention in a culture medium, to allow L-proline to be produced and accumulated in the culture medium, and collecting L-proline from the culture medium. Also, the method of present invention includes method for producing L-leucine, comprising steps of cultivating the bacterium of the present invention in a culture medium, to allow L-leucine to be produced and accumulated in the culture medium, and collecting L-leucine from the culture medium. And, the method of present invention includes method for producing L-methionine, comprising steps of cultivating the bacterium of the present invention in a culture medium, to allow L-methionine to be produced and accumulated in the culture medium, and collecting L-methionine from the culture medium.

The method of the present invention also includes method for producing L-threonine, comprising steps of cultivating the bacterium of the second embodiment of the present invention in a culture medium, to allow L-threonine to be produced and accumulated in the culture medium, and collecting L-threonine from the culture medium. Also the method of present invention includes method for producing L-valine, comprising steps of cultivating the bacterium of the present invention in a culture medium, to allow L-valine to be produced and accumulated in the culture medium, and collecting L-valine from the culture medium.

The method of present invention further includes method for producing L-arginine, comprising steps of cultivating the bacterium of the third embodiment of the present invention in a culture medium, to allow L-arginine to be produced and accumulated in the culture medium, and collecting L-arginine from the culture medium. Also, the method of present invention includes method for producing L-proline, comprising steps of cultivating the bacterium of the present invention in a culture medium, to allow L-proline to be produced and accumulated in the culture medium, and collecting L-proline from the culture medium.

In the present invention, the cultivation, the collection and purification of L-amino acid from the medium and the like may be performed in a manner similar to the conventional fermentation method wherein an amino acid is produced using a microorganism. A medium used for culture may be either a synthetic medium or a natural medium, so long as the medium includes a carbon source and a nitrogen source and minerals and, if necessary, appropriate amounts of nutrients which the microorganism requires for growth. The carbon source may include various carbohydrates such as glucose and sucrose, and various organic acids. Depending on the mode of assimilation of the used microorganism, alcohol including ethanol and glycerol may be used. As the nitrogen source, various ammonium salts such as ammonia and ammonium sulfate, other nitrogen compounds such as amines, a natural nitrogen source such as peptone, soybean-hydrolysate and digested fermentative microorganism are used. As minerals, potassium monophosphate, magnesium sulfate, sodium chloride, ferrous sulfate, manganese sulfate, calcium chloride, and the like are used.

The cultivation is performed preferably under aerobic conditions such as a shaking culture, and stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to the accumulation of the target L-amino acid in the liquid medium.

After cultivation, solids such as cells can be removed from the liquid medium by centrifugation or membrane filtration, and then the target L-amino acid can be collected and purified by ion-exchange, concentration and crystallization methods.

BEST MODE FOR CARRYING OUT THE INVENTION

Figure 1:
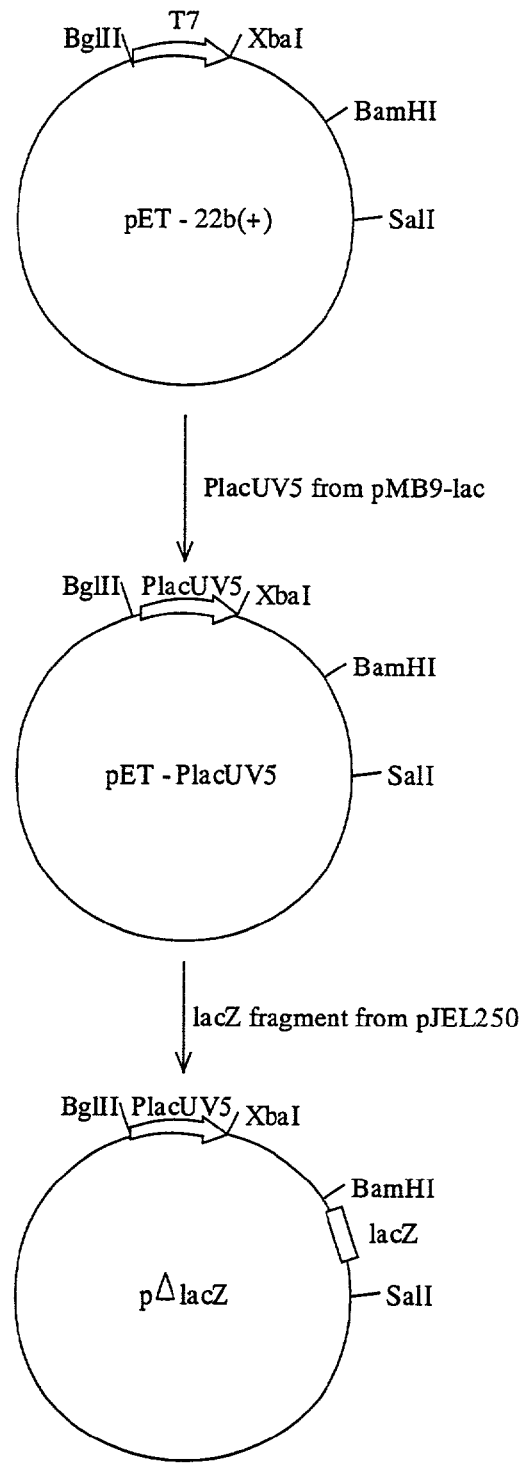
FIG. 1 shows the construction of plasmid pΔlacZ.

The present invention will be more concretely explained below with reference to Examples. In the Examples an amino acid is of L-configuration unless otherwise noted.

EXAMPLE 1

Cloning of the b2682, b2683, b1242, and b3434 Genes on the Plasmid pΔlacZ

For cloning of the b2682 and b2683 genes vector pΔlacZ was used. Vector pΔlacZ is a derivative of the vector pET-22b (+) (Novagen, Madison, Wis., USA). pET-22b(+) was treated by BglII and XbaI and ligated with polymerase chain reaction (PCR) fragment of plasmid pMB9-lac (Fuller F., *Gene*, 19, 43-54, 1982) treated with the same restrictases and carried $P_{lac}$ UV5 promoter. For amplifying the $P_{lac}$ UV5 promoter fragment by PCR primers having sequence depicted in SEQ ID Nos: 7 and 8 were used. The resulted plasmid was supplemented with structural part of lacZ gene (237 bp without promoter) by cloning SalI-BamHI fragment of the plasmid pJEL250 (Dymakova E. et al., *Genetika* (rus), 35, 2, 181-186, 1999). Scheme for obtaining vector pΔlacZ is shown in FIG. 1.

The initial material for cloning of *E. coli* b2682 and b2683 putative reading frames (b2682 and b2683 genes) was the PCR fragment, which was obtained using DNA from *E. coli* strain TG1 as a template. For synthesis of this fragment two primers having sequence depicted in SEQ ID Nos: 1 and 2 were used. PCR was carried out on "Perkin Elmer GeneAmp PCR System 2400" under the following conditions: 40 sec. at 95° C., 40 sec. at 47° C., 40 sec. at 72° C., 30 cycles. Thus, the 1158 bp linear DNA fragment contained b2682 and b2683 genes was obtained. This PCR fragment was treated by XbaI and BamHI restrictases and inserted into multicopy vector pΔlacZ previously treated by the same restrictases.

Resulted plasmid with the PCR fragment was named pYGAZH and carried both gene b2682 and b2683 under the control of the lactose promoter ($P_{lac}$ UV5).

Similarly, the initial material for cloning of *E. coli* b1242 putative reading frame (b1242 gene) was the PCR fragment, which was obtained using DNA from *E. coli* strain TG1 as a template. For synthesis of this fragment two primers having sequence depicted in SEQ ID Nos: 9 and 10 were used. Resulted plasmid with the PCR fragment was named pYCHE and carried b1242 gene under the control of the lactose promoter ($P_{lac}$ UV5). The initial material for cloning of *E. coli* b3434 putative reading frame (b3434 gene) was the PCR fragment, which was obtained using DNA from *E. coli* strain TG1 as a template. For synthesis of this fragment two primers having sequence depicted in SEQ ID Nos: 13 and 14 were used. Resulted plasmid with the PCR fragment was named pYHGN and carried b3434 gene under the control of the lactose promoter ($P_{lac}$ UV5).

EXAMPLE 2

The Influence of the Amplified b2682 and b2683 Genes on Resistance of E. coli Strain TG1 to Amino Acids and its Analogs E. coli strain TG1(pYGAZH), TG1(pYCHE), TG1(pYHGN) and TG1 strain having a vector without insertion (control strain) were grown overnight on LB medium supplemented with ampicilline (100 μg/ml). The night cultures of all strains were diluted at 25 times in fresh LB medium supplemented with ampicilline (100 μg/ml) and IPTG (0.5 mM) and were incubated 2 hours at 37° C. with aeration. The log phase cultures were diluted in 0.9% solution of NaCl and about 1000 cells were seeded on plates with solid Adams medium supplemented with ampicilline (100 μg/ml), IPTG (0.5 mM) and amino acid or its analog. After 2-4 days incubation at 37° C. the differences in colony size or colony number between the TG1 strain with hybrid plasmid and control TG1 strain were registered. The results of experiments are presented in Table 1.

TABLE 1

| Inhibitors | Concentration in media, μg/ml | Effect on the growth of TG1 strain having plasmid | | |
|---|---|---|---|---|
| | | pYGAZH | pYCHE | pYHGN |
| Proline | 30000 | No | No | No |
| 3,4-Dihydroproline | 23 | R | No | No |
| Isoleucine | 18000 | No | No | No |
| DL-Thiaisoleucine | 1 | R | No | No |
| o-Methylthreonine | 6 | No | No | No |
| L-Serine | 2800 | No | No | No |
| DL-Serine | 3600 | No | No | No |
| DL-Serine hydroxamate | 140 | No | No | No |
| DL-o-Methylserine | 3200 | R | R | R |
| 4-Azaleucine | 45 | R | No | No |
| 6-Diazo-5-oxo-L-norleucine | 15 | No | No | R |
| Valine | 7 | R | No | No |
| Methionine | 38000 | No | No | No |
| Norleucine | 500 | R | No | No |
| Cysteine | 1600 | No | No | No |
| Homoserine | 1000 | No | R | No |
| DL-β-Hydroxy-norvaline | 80 | No | No | R |
| L-Aspartic acid β-hydroxamate | 100 | No | No | No |
| Arginine | 4300 | No | No | No |
| Lysine | 5000 | No | No | No |
| S-(2-Aminoethyl)cysteine | 0.75 | No | No | S |
| Histidine | 3000 | No | No | No |
| L-Histidine hydroxamate | 200 | No | No | No |
| DL-1,2,4-Triazole-3-alanine | 80 | No | No | No |
| Phenylalanine | 13000 | No | No | No |
| p-Fluorophenylalanine | 6 | No | No | No |
| L-o-Fluorophenylalanine | 1.7 | R | No | No |
| DL-o-Fluorophenylalanine | 6 | R | No | No |
| Tryptophan | 12500 | No | No | No |
| DL-4-Fluorotryptophan | 0.1 | No | No | No |
| 4-Methyltryptophan | 0.25 | No | No | No |
| 7-Methyltryptophan | 100 | No | No | No |
| DL-a-Methyltryptophan | 400 | No | No | No |
| m-Fluoro-DL-tyrosine | 0.5 | No | No | No |

No—no differences compare to the control strain
R—more colonies or colony size
S—less colonies or colony size compare to the control strain

EXAMPLE 3

Production of Threonine by a Strain having Plasmid pYGAZH

The threonine producing strain VL2054 was transformed by the plasmid pYGAZH carried the b2682 and b2683 genes under the control of $P_{lac}$ UV5 promoter. Obtained strain was named VL2054(pYGAZH). The strain VL2054 is derivative of the strain VKPM B-3996 and carried on its chromosome:

a) the integrated threonine operon under the control of $P_R$ promoter b) wild type rhtA gene c) the inactivated chromosomal gene encoding transhydrogenase (tdh gene) and inactivated kanamycin resistant gene (kan) gene in the Tn5 (tdh::Tn5, Kan$^s$)

d) mutation ilvA$_{442}$.

The strain VL2054 has been deposited in the Russian National Collection of Industrial Microorganisms (VKLPM) (Russia 113545, Moscow, 1 Dorozbny proezd, 1) on Jan. 30, 2001 under accession number VKIPM B-8067, and transferred from the original deposit to international deposit based on Budapest Treaty on Feb. 1, 2002.

The 5 colonies of each strain VL2054, strain VL2054(pΔ-lacZ) as a control strain contained plasmid without insertion and VL2054(pYGAZH) were suspended in 2 ml of minimal medium (($NH_4)_2SO_4$—11 g/l; NaCl—0.4 g/l; $MgSO_4$—0.4 g/l; $K_2HPO_4$—1 g/l; $FeSO_4$—10 mg/l; $MnSO_4$—10 mg/l; thiamin—0.1 mg/l; yeast extract—0.5 g/l; glucose—40 g/l; ampicilline—300 mg/l if necessary) in 20-ml test tubes and were incubated overnight with aeration at 32° C. The 0.2 ml of each night culture was transferred to the three 20-ml test tubes with 2 ml of fresh medium for fermentation with or without IPTG and cultivated at 32° C. for 48 or 72 hours with rotary shaker.

Fermentation Medium Composition:

| | |
|---|---|
| $(NH_4)_2SO_4$ | 22 g/l |
| NaCl | 0.8 g/l |
| $MgSO_4$ | 0.8 g/l |
| $K_2HPO_4$ | 2 g/l |
| $FeSO_4$ | 20 mg/l |
| $MnSO_4$ | 20 mg/l |
| Thiamin | 0.2 mg/l |
| Yeast extract | 1 g/l |
| $CaCO_3$ | 30 g/l |
| Glucose | 80 g/l |
| Ampicilline | 300 mg/l, if necessary |
| IPTG | 0.5 mM, if necessary |

After cultivation the plasmid stability and optical absorbance of the medium at 540 nm were determined by conventional methods. Accumulated amount of threonine in the medium was determined by thin layer chromatography (TLC). Liquid phase composition for TLC was as follows: isopropanol—50 ml, acetone—50 ml, $NH_4OH$ (30%)—12 ml, $H_2O$—8 ml. The results are shown in Table 2. As it is seen, the hybrid plasmid pYGAZH improved the threonine accumulation by the threonine producing strain VL2054.

TABLE 2

| VL2054 with plasmid | IPTG | 48 hours | | | 72 hours | | |
|---|---|---|---|---|---|---|---|
| | | OD$_{540}$ | Thr, g/l | Thr/OD | OD$_{540}$ | Thr, g/l | Thr/OD |
| no | − | 19 | 5.2 | 0.27 | 26 | 9.1 | 0.35 |
| | + | 21 | 4.1 | 0.20 | 29 | 7.8 | 0.27 |
| pΔlacZ | − | 20 | 6.4 | 0.32 | 24 | 9.1 | 0.40 |
| | + | 15 | 3.5 | 0.23 | 24 | 7.2 | 0.30 |
| pYGAZH | − | 17 | 5.7 | 0.34 | 24 | 9.7 | 0.40 |
| | + | 21 | 9.8 | 0.47 | 23 | 15.5 | 0.67 |

EXAMPLE 4

Production of Valine by a Strain having Plasmid pYGAZH

The valine producing strain H-81 was transformed by the plasmid pYGAZH carrying the b2682 and b2683 genes under the control of the P$_{1ac}$UV5 promoter. The strain H-81 has been deposited in the Russian National Collection of Industrial Microorganisms (VKPM) (Russia 113545, Moscow, 1 Dorozhny proezd, 1) on Jan. 30, 2001 under accession number VKPM B-8066, and transferred from the original deposit to international deposit based on the Budapest Treaty on Feb. 1, 2002.

The 5 colonies of each strain H-81, H-81(pΔlacZ) as a control strain contained plasmid without insertion and H-81 (pYGAZH) were suspended in 2 ml of minimal medium ((NH$_4$)$_2$SO$_4$—18 g/l, K$_2$HPO$_4$—1.8 g/l, MgSO$_4$—1.2 g/l, thiamin—0.1 mg/l, yeast extract—0.5 g/l, glucose—60 g/l, ampicilline—300 mg/l, if necessary) in 20-ml test tubes and were incubated overnight with aeration at 32° C. The 0.2 ml of each night culture was transferred to the three 20-ml test tubes with 2 ml of fresh medium for fermentation with or without IPTG and cultivated at 32° C. for 48 or 72 hours with rotary shaker.

Fermentation Medium Composition:

| | |
|---|---|
| (NH$_4$)$_2$SO$_4$ | 18 g/l, |
| K$_2$HPO$_4$ | 1.8 g/l, |
| MgSO$_4$ | 1.2 g/l, |
| CaCO$_3$ | 20 g/l, |
| Thiamin | 0.1 mg/l, |
| Glucose | 60 g/l, |
| Ampicilline | 300 mg/l, if necessary |
| IPTG | 0.5 mM, if necessary |

After cultivation the plasmid stability and optical absorbance of the medium at 540 nm were determined by conventional methods. Accumulated amount of valine in the medium was determined by TLC. Liquid phase composition for TLC was as follows: isopropanol—80 ml, ethylacetate—80 ml, NH$_4$OH (30%)—15 ml, H$_2$O—45 ml. The results are shown in Table 3. As it is seen, the hybrid plasmid pYGAZH improved the valine accumulation by the valine producing strain H-81.

TABLE 3

| H-81 with plasmid | IPTG | 48 hours | | | 72 hours | | |
|---|---|---|---|---|---|---|---|
| | | OD$_{540}$ | Val, g/l | Val/OD | OD$_{540}$ | Val, g/l | Val/OD |
| No | − | 34 | 11.6 | 0.34 | 32 | 10.3 | 0.32 |
| | + | 34 | 11.7 | 0.34 | 30 | 10.1 | 0.34 |
| pΔlacZ | − | 34 | 10.5 | 0.31 | 30 | 10.0 | 0.33 |
| | + | 20 | 7.8 | 0.39 | 25 | 9.0 | 0.36 |
| pYGAZH | − | 29 | 10.5 | 0.36 | 31 | 12.8 | 0.41 |
| | + | 22 | 10.8 | 0.49 | 23 | 12.3 | 0.53 |

REFERENCE EXAMPLE 1

Production of L-Proline by an ilvA Deficient L-Proline Producer

The cells of wild type strain *E. coli* K12 (VKPM B-7) was treated with a mutagen, N-methyl-N'-nitro-N-nitrosoguanidine (0.1 mg/ml), for 20 min at 37° C., washed and plated on minimal agar medium M9 supplemented with 1.25 mg/ml tryptone, 10 mg/ml L-proline and 0.05 mg/ml 2,3,5-triphenyltetrazolium chloride. Most colonies arisen after 3 day of incubation at 37° C. were colored red. A few colonies, which could not oxidize L-proline, were white. One of such colonies was used as a parent for obtaining mutants resistant to proline analogs (3,4-dehydroxyproline and azetidine-2-carboxylate) which were added into M9 agar medium in concentration of 2 mg/ml each.

Some of mutants arisen could produce L-proline. The best L-proline producer 702 was treated with a P1 bacteriophage grown on cells of the strain TG1 in which the gene ilvA was disrupted by the insertion of chloramphenicol (Cm) resistance (Cm$^r$) gene. One of obtained Cm resistant transductant, 702ilvA, which turned to be L-isoleucine auxotroph, was much more effective L-proline producer than the L-isoleucine prototrophic parent strain 702 (Table 4). The fermentation medium contained 60 g/l glucose, 25 g/l ammonium sulfate, 2 g/l KH$_2$PO$_4$, 1 g/l MgSO$_4$, 0.1 mg/l thiamine, 50 mg/l L-isoleucine and 25 g/l chalk (pH 7.2). Glucose and chalk were sterilized separately. 2 ml of the medium was placed into test tubes, and inoculated with one loop of the tested microorganisms, and the cultivation was carried out at 37° C. for 2 days with shaking.

TABLE 4

| Strain | Phenotype | Accumulation of L-proline (g/l) |
|---|---|---|
| K12 (VKPM B-7) | Wild type | <0.1 |
| 702 (VKPM B-8011) | Defective L-proline degradation, resistance to proline analogs | 0.5 |
| 702ilvA (VKPM B-8012) | Defective L-proline degradation, resistance to proline analogs, L-isoleucine auxotroph, Cm$^r$ | 8.0 |

The strains 702 and 702ilvA have been deposited in the Russian National Collection of Industrial Microorganisms (VKPM) under the accession number VKPM B-8011 and VKPM B-8012, respectively, since Jul. 25, 2000.

EXAMPLE 5

Production of Proline by a Strain having Plasmid pYGAZH

The proline producing strain *E. coli* 702ilvA was transformed by the plasmid pYGAZH carried the b2682 and b2683 genes under the control of $P_{lac}$ UV5 promoter.

The 5 colonies of each strain 702ilvA, 702ilvA(pΔlacZ) as a control strain contained plasmid without insertion and 702ilvA(pYGAZH) were suspended in 2 ml of minimal medium ((NH$_4$)$_2$SO$_4$—18 g/l, K$_2$HPO$_4$—1.8 µl, MgSO$_4$—1.2 g/l, thiamin—0.1 mg/l, yeast extract—0.5 g/l, glucose—60 g/l, isoleucine—50 mg/l, ampicilline—300 mg/l, if necessary) in 20-ml test tubes and were incubated overnight with aeration at 32° C. The 0.2 ml of each night culture was transferred to the three 20-ml test tubes with 2 ml of fresh medium for fermentation with or without IPTG and cultivated at 32° C. for 40 hours with rotary shaker.

Fermentation Medium Composition:

| | |
|---|---|
| (NH$_4$)$_2$SO$_4$ | 18 g/l, |
| K$_2$HPO$_4$ | 1.8 g/l, |
| MgSO$_4$ | 1.2 g/l, |
| CaCO$_3$ | 20 g/l, |
| Thiamin | 0.1 mg/l, |
| Glucose | 60 g/l, |
| Isoleucine | 50 mg/l |
| Ampicilline | 300 mg/l, if necessary |
| IPTG | 0.5 mM, if necessary |

After cultivation the plasmid stability and optical absorbance of the medium at 540 nm were determined by conventional methods. Accumulated amount of proline in the medium was determined by TLC. Liquid phase composition for TLC was as follows: ethanol—80 ml, NH$_4$OH (30%)—5 ml, H$_2$O—25 ml. The results are shown in Table 5. As it is seen, the hybrid plasmid pYGAZH improved the proline accumulation by the proline producing strain 702ilvA.

TABLE 5

| 702ilvA with plasmid | IPTG | 40 hours | | |
|---|---|---|---|---|
| | | OD$_{540}$ | Pro, g/l | Pro/OD |
| No | − | 25 | 4.0 | 0.16 |
| | + | 23 | 4.1 | 0.18 |
| pΔlacZ | − | 24 | 5.3 | 0.22 |
| | + | 22 | 5.0 | 0.23 |
| pYGAZH | − | 21 | 5.0 | 0.24 |
| | + | 23 | 10.6 | 0.46 |

REFERENCE EXAMPLE 2

Production of L-Leucine by an ilvE Deficient L-Leucine Producer

The cells of wild type strain *E. coli* K12 (VKPM B-7) was treated with a mutagen, N-methyl-N'-nitro-N-nitrosoguanidine (0.05 mg/ml), for 20 min at 37° C., washed 4 times with physiological solution and plated on minimal agar medium M9 supplemented with 4.0 DL-4-azaleucine. The plates were incubated for 5 days at 37° C. Colonies appeared on the plates were picked up and purified by streaking on the L-agar plates. One of the obtained mutant resistant to DL-4-azaleucine was used for induction of double L-isoleucine and L-valine auxotrophy. The numerous amount of double auxotrophs, requiring L-isoleucine and L-valine for growth, were obtained. It was shown that double L-isoleucine and L-valine auxotrophy was caused by mutation in the ilvE gene. Among the obtained double auxotrophs, the best L-leucine producer, strain 505 producing 1.8 g/l of L-leucine, has been selected. The fermentation medium contained 60 g/l glucose, 25 g/l ammonium sulfate, 2 g/l KH$_2$PO$_4$, 1 g/l MgSO$_4$, 0.1 mg/l thiamine, 100 mg/l L-isoleucine, 100 mg/l L-valine and 25 g/l chalk (pH 7.2). Glucose and chalk were sterilized separately. 2 ml of the medium was placed into test tubes, and inoculated with one loop of the tested microorganisms, and the cultivation was carried out at 37° C. for 2 days with shaking.

The strain *E. coli* 505 has been deposited in the Russian National Collection of Industrial Microorganisms (VKPM) (Russia 113545, Moscow, 1 Dorozhny proezd, 1) on May 14, 2001 under accession number VKPM B-8124, and transferred from the original deposit to international deposit based on the Budapest Treaty on Feb. 1, 2002.

EXAMPLE 6

Production of Leucine by a Strain having Plasmid pYGAZH

The leucine producing strain *E. coli* 505 was transformed by the plasmid pYGAZH carried the b2682 and b2683 genes under the control of $P_{lac}$ UV5 promoter.

The 20 colonies of each strain 505, 505(pΔlacZ) as a control strain contained plasmid without insertion and 505 (pYGAZH) were transferred by one loop of culture in 20-ml test tubes with L-broth with or without ampicilline and were incubated overnight with aeration at 32° C. The 0.1 ml of each night culture was transferred into the 20-ml test tubes (inner diameter 22 mm), suspended in 2 ml of medium for fermentation with or without IPTG and cultivated at 32° C. for 72 hours with rotary shaker.

Fermentation Medium Composition:

| | |
|---|---|
| (NH$_4$)$_2$SO$_4$ | 15 g/l, |
| K$_2$HPO$_4$ | 1.5 g/l, |
| MgSO$_4$ × 7H$_2$O | 1.0 g/l, |
| CaCO$_3$ | 20 g/l (sterilized separately), |
| Thiamin | 0.1 mg/l, |
| Glucose | 60 g/l (sterilized separately), |
| Isoleucine | 0.3 g/l |
| Valine | 0.3 g/l |
| Ampicilline | 150 mg/l, if necessary |
| IPTG | 0.5 mM, if necessary |

After cultivation the plasmid stability was determined by conventional method. Accumulated amount of leucine in the medium was determined by TLC. Liquid phase composition for TLC was as follows: isopropanol—80 ml, ethylacetate—80 ml, NH$_4$OH (30%)—25 ml, H$_2$O—50 ml. The results are shown in Table 6. As it is seen, the hybrid plasmid pYGAZH improved the leucine accumulation by the leucine producing strain 505.

TABLE 6

| 505 with plasmid | IPTG | 72 hours Leu, g/l |
|---|---|---|
| No | − | 1.8 |
|  | + | 2.0 |
| pΔlacZ | − | 1.8 |
|  | + | 2.0 |
| pYGAZH | − | 2.0 |
|  | + | 2.8 |

REFERENCE EXAMPLE 3

Production of L-Methionine by L-Methionine Producer Resistant to Norleucine

The plasmidless threonine and leucine deficient strain E. coli C600 was used as a parental strain. At first, the Leu$^+$ variants of E. coli C$_{6-00}$ strain was obtained by transduction of phage P1 grown on E. coli K-12 strain. Then, after treatment with N-methyl-N'-nitro-N-nitrosoguanidine (NTG) the mutant strain 44 resistant to 8 g/l of L-homoserine has been obtained. The strain 44 is L-threonine-deficient, resistant to high concentrations of L-homoserine. The strain 44 has been deposited in Russian National Collection of Industrial Microorganisms (VKPM) under the accession number VKPM B-2175.

Then, the strains, which are the mutants resistant to a methionine analog, norleucine, was induced from strain 44 by mutagenesis using NTG. The cells of night culture grown in L-broth were spun down and resuspended in physiological solution (0.9% NaCl) containing 50 μg/ml of NTG. After 30 min of exposure with NTG at 37° C. the cells were spun down, washed 4 times with physiological solution and plated on the minimal agar medium M9, containing 0.5 mg/ml of threonine and 2.5 mg/ml or 5.0 mg/ml of norleucine. The plates were incubated for 5 days at 37° C. Colonies appeared on the plates were picked up and purified by streaking on the L-agar plates. The best L-methionine producer among them was strain 218. Test-tube cultivation of the novel strain 218 carried out at 32° C. for 3 days with shaking leads to accumulation in the culture medium about 1 g/l of L-methionine. As a fermentation medium was used minimal medium M9 containing glucose (4%), ammonia sulfate (2.5%), threonine (0.5 g/l), calcium carbonate (25 g/l). Glucose and chalk were sterilized separately.

The strain 218 has been deposited in the Russian National Collection of Industrial Microorganisms (VKPM) (Russia 113545, Moscow 1, Dorozhny proezd, 1) under the accession number VKPM B-8 125 since May 14, 2001, and transferred from the original deposit to international deposit based on the Budapest Treaty on Feb. 1, 2002.

Further, the phage P1 mediated deletion of ppc gene has been introduced into strain 218 followed by integration of pycA gene from Bacillus subtilis (Russian patent application 99121636). Resulted strain 218pycA lost resistance to norleucine. Therefore, resistance to norleucine has been imparted to the strain again as described above. The best L-methionine producer among obtained strains was strain E. coli 73 which produced about 1 g/l of L-methionine under condition described above.

The strain E. coli 73 has been deposited in the Russian National Collection of Industrial Microorganisms (VKPM) (Russia 113545, Moscow 1, Dorozhny proezd, 1) on May 14, 2001 under accession number VKPM B-8126, and transferred from the original deposit to international deposit based on the Budapest Treaty on Feb. 1, 2002.

EXAMPLE 7

Production of Methionine by a Strain having Plasmid pYGAZH

The methionine producing strain E. coli 73 was transformed by the plasmid pYGAZH carried the b2682 and b2683 genes under the control of P$_{lac}$ UV5 promoter.

The 5 colonies of each strain 73, 73(pΔlacZ) as a control strain contained plasmid without insertion and 73(pYGAZH) were suspended in 2 ml of minimal medium (($NH_4$)$_2SO_4$—18 g/l, $K_2HPO_4$—1.8 g/l, $MgSO_4$—1.2 g/l, thiamin—0.1 mg/l, yeast extract—10 g/l, glucose—60 g/l, threonine—400 mg/l, ampicilline—300 mg/l, if necessary) in 20-ml test tubes and were incubated overnight with aeration at 32° C. The 0.2 ml of each night culture was transferred to the three 20-ml test tubes with 2 ml of fresh medium for fermentation with or without IPTG and cultivated at 32° C. for 48 hours with rotary shaker.

Fermentation Medium Composition:

| ($NH_4$)$_2SO_4$ | 18 g/l, |
| $K_2HPO_4$ | 1.8 g/l, |
| $MgSO_4$ | 1.2 g/l, |
| $CaCO_3$ | 20 g/l, |
| Thiamin | 0.1 mg/l, |
| Glucose | 60 g/l, |
| Threonine | 400 mg/l, |
| Yeast extract | 1.0 g/l, |
| Ampicilline | 300 mg/l, if necessary |
| IPTG | 0.5 mM, if necessary |

After cultivation the plasmid stability and optical absorbance of the medium at 540 nm were determined by conventional methods. Accumulated amount of methionine in the medium was determined by TLC. Liquid phase composition for TLC was as follows: isopropanol—80 ml, ethylacetate—80 ml, $NH_4OH$ (30%)—15 ml, $H_2O$—45 ml. The results are shown in Table 7. As it is seen, the hybrid plasmid pYGAZH improved the methionine accumulation by the methionine producing strain 73.

TABLE 7

| 73 with plasmid | IPTG | 48 hours | | |
|---|---|---|---|---|
|  |  | $OD_{540}$ | Met, g/l | Met/OD |
| No | − | 45 | 0.7 | 0.016 |
|  | + | 42 | 1.1 | 0.026 |
| pΔlacZ | − | 45 | 1.0 | 0.022 |
| pYGAZH | − | 48 | 0.9 | 0.019 |
|  | + | 46 | 1.3 | 0.028 |

EXAMPLE 8

Production of Threonine by a Strain having Plasmid pYCHE

The threonine producing strain VL2054 was transformed by the plasmid pYCHE carried the b1242 gene under the control of P$_{lac}$ UV5 promoter. Obtained strain was named VL2054(pYCHE).

The 5 colonies of each strain VL2054, strain VL2054(pΔ-lacZ) as a control strain contained plasmid without insertion and VL2054(pYCHE) were suspended in 2 ml of minimal medium (($NH_4$)$_2$$SO_4$—11 g/l; NaCl—0.4 g/l; $MgSO_4$—0.4 g/l; $K_2HPO_4$—1 g/l; $FeSO_4$—10 mg/l; $MnSO_4$—10 mg/l; thiamin—0.1 mg/l; yeast extract—0.5 g/l; glucose—40 g/l; ampicilline—300 mg/l if necessary) in 20-ml test tubes and were incubated overnight with aeration at 32° C. The 0.2 ml of each night culture was transferred to the three 20-ml test tubes with 2 ml of fresh medium for fermentation with or without IPTG and cultivated at 32° C. for 45 hours with rotary shaker.

Fermentation Medium Composition:

| | |
|---|---|
| ($NH_4$)$_2$$SO_4$ | 22 g/l |
| NaCl | 0.8 g/l |
| $MgSO_4$ | 0.8 g/l |
| $K_2HPO_4$ | 2 g/l |
| $FeSO_4$ | 20 mg/l |
| $MnSO_4$ | 20 mg/l |
| Thiamin | 0.2 mg/l |
| Yeast extract | 1 g/l |
| $CaCO_3$ | 30 g/l |
| Glucose | 80 g/l |
| Ampicilline | 300 mg/l, if necessary |
| IPTG | 0.5 mM, if necessary |

After cultivation the plasmid stability and optical absorbance of the medium at 540 nm were determined by conventional methods. Accumulated amount of threonine in the medium was determined by thin layer chromatography (TLC). Liquid phase composition for TLC was as follows: isopropanol—50 ml, acetone—50 ml, $NH_4OH$ (30%)—12 ml, $H_2O$—8 ml. The results are shown in Table 8. As it is seen, the hybrid plasmid pYCHE improved the threonine accumulation by the threonine producing strain VL2054.

TABLE 8

| VL2054 with plasmid | IPTG | $OD_{540}$ | Thr, g/l | Thr/OD |
|---|---|---|---|---|
| no | − | 21 | 4.8 | 0.23 |
| | + | 20 | 4.7 | 0.24 |
| pΔlacZ | − | 16 | 4.6 | 0.29 |
| | + | 13 | 3.0 | 0.23 |
| pYCHE | − | 20 | 6.2 | 0.31 |
| | + | 20 | 7.0 | 0.35 |

EXAMPLE 9

Production of Valine by a Strain having Plasmid pYCHE

The valine producing strain H-81 was transformed by the plasmid pYCHE carried the b1242 gene under the control of $P_{lac}$ UV5 promoter.

The 5 colonies of each strain H-81, H-81(pΔlacZ) as a control strain contained plasmid without insertion and H-81 (pYCHE) were suspended in 2 ml of minimal medium (($NH_4$)$_2$ $SO_4$—18 g/l, $K_2HPO_4$—1.8 g/l, $MgSO_4$—1.2 g/l, thiamin—0.1 mg/l, yeast extract—0.5 g/l, glucose—60 g/l, ampicilline—300 mg/l, if necessary) in 20-ml test tubes and were incubated overnight with aeration at 32° C. The 0.2 ml of each night culture was transferred to the three 20-ml test tubes with 2 ml of fresh medium for fermentation with or without IPTG and cultivated at 32° C. for 45 hours with rotary shaker.

Fermentation Medium Composition:

| | |
|---|---|
| ($NH_4$)$_2$$SO_4$ | 18 g/l, |
| $K_2HPO_4$ | 1.8 g/l, |
| $MgSO_4$ | 1.2 g/l, |
| $CaCO_3$ | 20 g/l, |
| Thiamin | 0.1 mg/l, |
| Glucose | 60 g/l, |
| Ampicilline | 300 mg/l, if necessary |
| IPTG | 0.5 mM, if necessary |

After cultivation the plasmid stability and optical absorbance of the medium at 540 nm were determined by conventional methods. Accumulated amount of valine in the medium was determined by TLC. Liquid phase composition for TLC was as follows: isopropanol—80 ml, ethylacetate—80 ml, $NH_4OH$ (30%)—15 ml, $H_2O$—45 ml. The results are shown in Table 9. As it is seen, the hybrid plasmid pYCHE improved the valine accumulation by the valine producing strain H-81.

TABLE 9

| H-81 with plasmid | IPTG | $OD_{540}$ | Val, g/l | Val/OD |
|---|---|---|---|---|
| no | − | 34 | 11.6 | 0.34 |
| | + | 34 | 11.7 | 0.34 |
| pΔlacZ | − | 34 | 10.5 | 0.31 |
| | + | 20 | 7.8 | 0.39 |
| pYCHE | − | 32 | 14.0 | 0.44 |
| | + | 30 | 13.9 | 0.46 |

EXAMPLE 10

Production of Arginine by a Strain having Plasmid pYHGN

The arginine producing strain 382 was transformed by the plasmid pYHGN carried the b3434 gene under the control of $P_{lac}$ UV5 promoter. The strain 382 has been deposited in the Russian National Collection of Industrial Microorganisms (VKPM) (Russia 113545, Moscow, 1 Dorozhny proezd, 1) on Apr. 10, 2000 under accession number VKPM B-7926.

The 5 colonies of each strain 382, 382(pΔlacZ) as a control strain contained plasmid without insertion and 382(pYHGN) were suspended in 2 ml of minimal medium (($NH_4$)$_2$$SO_4$—25.0 g/l, $K_2HPO_4$—2.0 g/l, $MgSO_4$ $7H_2O$—1.0 g/l, thiamin—0.2 mg/l, yeast extract—5 g/l, glucose—60 g/l, ampicilline—100 mg/l, if necessary) in 20-ml test tubes and were incubated overnight with aeration at 32° C. The 0.2 ml of each night culture was transferred to the three 20-ml test tubes with 2 ml of fresh medium for fermentation with or without IPTG and cultivated at 32° C. for 72 hours with rotary shaker.

Fermentation Medium Composition:

| | |
|---|---|
| $(NH_4)_2SO_4$ | 25 g/l, |
| $K_2HPO_4$ | 2.0 g/l, |
| $MgSO_4\ 7H_2O$ | 1.0 g/l, |
| Thiamin | 0.2 mg/l, |
| Yeast extract | 5 g/l |
| Glucose | 60 g/l, |
| $CaCO_3$ | 20 g/l |
| Ampicilline | 100 mg/l, if necessary |
| IPTG | 0.5 mM, if necessary |

After cultivation the plasmid stability and optical absorbance of the medium at 540 nm were determined by conventional methods. Accumulated amount of arginine in the medium was determined by TLC. Liquid phase composition for TLC was as follows: isopropanol—80 ml, ethylacetate—40 ml, $NH_4OH$ (30%)—25 ml, $H_2O$—50 ml. The results are shown in Table 10. As it is seen, the hybrid plasmid pYHGN improved the arginine accumulation by the arginine producing strain 382.

TABLE 10

| E. coli 382 with plasmid | IPTG | $OD_{540}$ | Arg, g/l | Arg/OD |
|---|---|---|---|---|
| No | − | 20 | 8.5 | 0.43 |
| | + | 22 | 6.7 | 0.31 |
| pΔlacZ | − | 28 | 6.3 | 0.23 |
| | + | 26 | 5.4 | 0.21 |
| pYHGN | − | 24 | 5.8 | 0.24 |
| | + | 26 | 9.3 | 0.36 |

EXAMPLE 11

Production of Proline by a Strain having Plasmid DYHGN

The proline producing strain E. coli 702ilvA was transformed by the plasmid pYHGN carried the b3434 gene under the control of $P_{lac}$ UV5 promoter.

The 5 colonies of each strain 702ilvA, 702ilvA(pΔlacZ) as a control strain contained plasmid without insertion and 702ilvA(pYHGN) were suspended in 2 ml of minimal medium (($NH_4)_2SO_4$—18 g/l, $K_2HPO_4$—1.8 g/l, $MgSO_4$—1.2 g/l, thiamin—0.1 mg/l, yeast extract—0.5 g/l, glucose—60 g/l, isoleucine—50 mg/l, ampicilline—300 mg/l, if necessary) in 20-ml test tubes and were incubated overnight with aeration at 32° C. The 0.2 ml of each night culture was transferred to the three 20-ml test tubes with 2 ml of fresh medium for fermentation with or without IPTG and cultivated at 32° C. for 40 hours with rotary shaker.

Fermentation Medium Composition:

| | |
|---|---|
| $(NH_4)_2SO_4$ | 18 g/l, |
| $K_2HPO_4$ | 1.8 g/l, |
| $MgSO_4$ | 1.2 g/l, |
| $CaCO_3$ | 20 g/l, |
| Thiamin | 0.1 mg/l, |
| Glucose | 60 g/l, |
| Isoleucine | 50 mg/l |
| Ampicilline | 300 mg/l, if necessary |
| IPTG | 0.5 mM, if necessary |

After cultivation the plasmid stability and optical absorbance of the medium at 540 nm were determined by conventional methods. Accumulated amount of proline in the medium was determined by TLC. Liquid phase composition for TLC was as follows: ethanol—80 ml, $NH_4OH$ (30%)—5 ml, $H_2O$—25 ml. The results are shown in Table 11. As it is seen, the hybrid plasmid pYHGN improved the proline accumulation by the proline producing strain 702ilvA.

TABLE 11

| 702ilvA with plasmid | IPTG | 40 hours | | |
|---|---|---|---|---|
| | | $OD_{540}$ | Pro, g/l | Pro/OD |
| No | − | 25 | 4.0 | 0.16 |
| | + | 23 | 4.1 | 0.18 |
| pΔlacZ | − | 24 | 5.3 | 0.22 |
| | + | 22 | 5.0 | 0.23 |
| pYHGN | − | 24 | 5.9 | 0.25 |
| | + | 17 | 7.1 | 0.42 |

Modifications and Other Embodiments

Various modifications and variations of the described products, compositions and methods as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the biochemical, chemical, chemical engineering, molecular biological, medical, or pharmacological arts or related fields are intended to be within the scope of the following claims.

INCORPORATION BY REFERENCE

Each document, patent application or patent publication cited by or referred to in this disclosure is incorporated by reference in its entirety. Any patent document to which this application claims priority is also incorporated by reference in its entirety. Specifically, priority documents Russian Patent Application No. 2001103865, filed Feb. 13, 2001; Russian Patent Application No. 2001104998, filed Feb. 26, 2001; Russian Patent Application No. 2001104999, filed Feb. 26, 2001; Russian Patent Application 2001117632, filed Jun. 28, 2001; and Russian Patent Application No. 2001117633, filed Jun. 28, 2001 are hereby incorporated by reference.

What is claimed is:

1. An isolated L-amino acid producing bacterium belonging to the genus *Eseherichia*, wherein the bacterium has increased expression of a gene encoding a protein selected from the group consisting of:

(A) a protein comprising the amino acid sequence in SEQ ID NO: 4; and (B) a protein comprising the amino acid sequence of SEQ ID NO: 4 except that a total of between 1 and 5 amino acids are deleted, substituted, inserted, or added, and wherein said protein imparts to the bacterium increased resistance to L-amino acids and/or analogs thereof;

and, in addition, increased expression of a gene encoding a protein selected from the group consisting of:

(C) a protein comprising the amino acid sequence in SEQ ID NO: 6 , and (D) a protein comprising the amino acid sequence of SEQ ID NO:6 except that a total of between 1 and 5 amino acids are deleted, substituted, inserted, or added, and wherein said protein imparts to the bacterium enhanced resistance to L-amino acids and/or analogs thereof, wherein the expression of said proteins is increased by transforming said bacterium with the gene coding for said protein, or by placing said gene under the control of a potent promoter.

2. The bacterium according to claim 1, wherein the transformation is performed with a multicopy vector.

3. A method for producing L-amino acid, which comprises cultivating the bacterium according to claim 1 in a culture medium and collecting from the culture medium L-amino acid to be produced and accumulated.

4. The method according to claim 3, wherein L-amino acid is L-threonine.

5. The method according to claim 4, wherein the bacterium has been modified so that the bacterium should have enhanced expression of threonine operon.

6. The method according to claim 3, wherein L-amino acid is L-valine.

7. The method according to claim 6, wherein the bacterium has been modified so that the bacterium should have enhanced expression of ilv operon.

8. The method according to claim 3, wherein L-amino acid is L-proline.

9. The method according to claim 8, wherein the bacterium has been modified so that the bacterium should have enhanced expression of genes for proline biosynthesis.

10. The method according to claim 3, wherein L-amino acid is L-leucine.

11. The method according to claim 10, wherein the bacterium has been modified so that the bacterium should have enhanced expression of leu operon.

12. The method according to claim 3, wherein L-amino acid is U-methionine.

13. The method according to claim 12, wherein the bacterium has been modified so that the bacterium should have enhanced expression of genes met regulon.

14. The bacterium according to claim 1, wherein the proteins (A) and (C) are encoded by the following polynucleotides, respectively;
   (a) the polynucleotide which has the nucleotide sequence of SEQ ID NO: 3,
   (c) the polynucleotide which has the nucleotide sequence of SEQ ID NO: 5.

15. The bacterium according to claim 1, wherein the proteins (B) and (D) are encoded by the following polynucleotide, respectively:
   (b) the polynucleotide which hybridizes with the sequence complementary to the nucleotide sequence of SEQ ID NO: 3 under conditions comprising washing in 1 ×SSC and 1% SDS 60° C., and
   (d) the polynucleotide which hybridizes with the sequence complementary to the nucleotide sequence of SEQ ID NO: 5 under conditions comprising washing in 1 ×SSC and 1% SDS 60° C.

16. A method for producing an L-amino acid comprising cultivating the bacterium according to claim 2 in a culture medium and collecting the L-amino acid from the culture medium.

* * * * *

UNITED STATES PATENT AND TRADEMARK OFFICE
CERTIFICATE OF CORRECTION

PATENT NO. : 7,476,531 B2  Page 1 of 1
APPLICATION NO. : 10/073293
DATED : January 13, 2009
INVENTOR(S) : Tabolina et al.

It is certified that error appears in the above-identified patent and that said Letters Patent is hereby corrected as shown below:

Claim 15, Col. 40 Line 9-17 should read

15. The bacterium according to claim 1, wherein the proteins (B) and (D) are encoded by the following polynucleotide, respectively:

(b) the polynucleotide which hybridizes with the sequence complementary to the nucleotide sequence of SEQ ID NO: 3 under conditions comprising washing in 1 × SSC and 0.1% SDS at 60° C., and (d) the polynucleotide which hybridizes with the sequence complementary to the nucleotide sequence of SEQ ID NO: 5 under conditions comprising washing in 1 × SSC and 0.1% SDS at 60° C.

Signed and Sealed this

Fourteenth Day of April, 2009

JOHN DOLL
*Acting Director of the United States Patent and Trademark Office*